(12) United States Patent
Chen et al.

(10) Patent No.: US 11,136,347 B2
(45) Date of Patent: Oct. 5, 2021

(54) CRYSTALLINE FORMS OF A FATTY ACID BILE ACID CONJUGATE, PREPARATION METHOD THEREOF AND USE THEREOF

(71) Applicant: Crystal Pharmaceutical (Suzhou) Co., Ltd., Jiangsu (CN)

(72) Inventors: Minhua Chen, Suzhou (CN); Yanfeng Zhang, Suzhou (CN); Chunxiang Huang, Suzhou (CN); Xiaoyu Zhang, Suzhou (CN)

(73) Assignee: Crystal Pharmaceutical (Suzhou) Co., Ltd., Suzhou (CN)

( * ) Notice: Subject to any disclaimer, the term of this patent is extended or adjusted under 35 U.S.C. 154(b) by 0 days.

(21) Appl. No.: 16/620,115

(22) PCT Filed: May 21, 2018

(86) PCT No.: PCT/CN2018/087680
§ 371 (c)(1),
(2) Date: Dec. 6, 2019

(87) PCT Pub. No.: WO2018/223836
PCT Pub. Date: Dec. 13, 2018

(65) Prior Publication Data
US 2021/0147471 A1    May 20, 2021

(30) Foreign Application Priority Data
Jun. 7, 2017  (CN) .......................... 201710423951.3

(51) Int. Cl.
*C07J 41/00* (2006.01)
*A61P 1/04* (2006.01)
*A61P 9/10* (2006.01)

(52) U.S. Cl.
CPC ............. *C07J 41/0005* (2013.01); *A61P 1/04* (2018.01); *A61P 9/10* (2018.01); *C07B 2200/13* (2013.01)

(58) Field of Classification Search
CPC .................. C07J 41/0005; C07B 2200/13
See application file for complete search history.

(56) References Cited

U.S. PATENT DOCUMENTS

2012/0277448 A1   11/2012   Jiang et al.

FOREIGN PATENT DOCUMENTS

| CN | 1296492 A | 5/2001 |
|---|---|---|
| CN | 105848718 A | 8/2016 |
| CN | 106496300 A | 3/2017 |
| WO | 1999/52932 A1 | 10/1999 |
| WO | 2015/083164 A1 | 6/2015 |

OTHER PUBLICATIONS

Bhattacharya et al. (Brittain, ed. Polymorphism in Pharmaceutical Solids, 2009, p. 334.*
International Search Report for Application No. PCT/CN2018/087680, dated Aug. 9, 2018, 6 pages.

* cited by examiner

*Primary Examiner* — Susanna Moore
(74) *Attorney, Agent, or Firm* — McCarter & English, LLP; Steven G. Davis; Wei Song

(57) ABSTRACT

The present disclosure relates to novel crystalline forms of compound (I) and processes for preparation and use thereof. Crystalline forms CS3, CS2, CS5 and CS8 of compound (I) of the present disclosure have advantages in at least one aspect of solubility, stability, melting point, hygroscopicity, particle size, bioavailability, processability, purification effect, flowability, adhesiveness, stability in drug product, in vitro and in vivo dissolution, etc., which provides new and better choices for preparation of drug product containing compound (I) and has significant values for future drug development.

Compound (I)

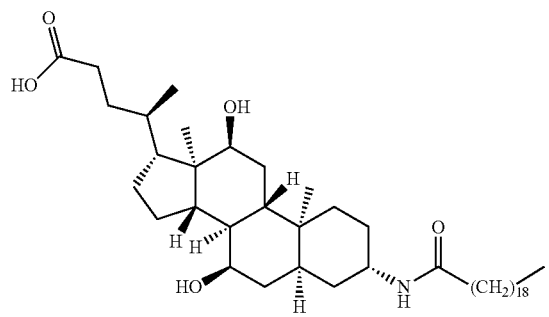

19 Claims, 26 Drawing Sheets

CRYSTALLINE FORMS OF A FATTY ACID BILE ACID CONJUGATE, PREPARATION METHOD THEREOF AND USE THEREOF

CROSS-REFERENCE TO RELATED APPLICATIONS

This application is an U.S. national stage application of PCT International Application No. PCT/CN2018/087680, filed on May 21, 2018, which claims the benefit of foreign priority of Chinese Patent Application No. 201710423951.3, filed on Jun. 7, 2017. The entire contents of the aforementioned applications are incorporated herein by reference.

TECHNICAL FIELD

The present disclosure relates to the field of pharmaceutical polymorph, particularly relates to novel crystalline forms of a fatty acid bile acid conjugate, processes for preparation and use thereof. The present disclosure belongs to the field of medicine.

BACKGROUND

Aramchol is a fatty acid bile acid conjugate, specifically an amide conjugate of arachidic acid and 3-aminocholic acid. Aramchol can effectively inhibit the activity of Stearoyl-CoA Desaturase1 (SCD1) related to fatty acid metabolism modulation. By inhibiting SCD1, Aramchol reduces the synthesis of fatty acids and increases β-oxidation, leading to decrease of triglycerides and fatty acid esters in live, therefore, reducing liver fat content effectively as well as improving metabolic parameters associated with fatty liver disease. Aramchol developed by Galmed Pharmaceuticals is used for treatment of fatty liver and Non Alcoholic Steatohepatitis in clinical development.

The chemical name of Aramchol is 3β-arachidylamido-7α,12α-dihydroxy-5β-cholan-24-oic acid (hereinafter referred to as "Compound (I)"), and the structure is shown as follows:

Compound (I)

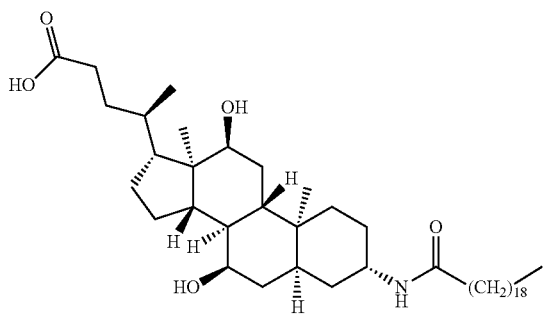

CN100386339C disclosed the process for preparing compound (I) without disclosure of any solid form. The inventors of the present disclosure have repeated the preparation method in CN100386339C and obtained an amorphous solid (the solid of the prior art). Further investigation indicates that the obtained amorphous solid has high hygroscopicity and poor stability, with a weight gain of 2.44% under 80% RH (Relative Humidity). Drugs substances with high hygroscopicity put a strict requirements on packaging and storage and imposes higher costs, which is not beneficial to production and applications. In order to overcome above-mentioned problems, the main objective of the present disclosure is to provide novel solid forms with excellent properties suitable for drug development. Through enormous experiments and research, the inventors of the present disclosure discovered crystalline forms CS2, CS3, CS5 and CS8 of compound (I). These crystalline forms have advantages in at least one aspect of solubility, stability, melting point, hygroscopicity, particle size, bioavailability, processability, purification effect, flowability, adhesiveness, formulation stability, in vitro and in vivo dissolution, etc. Particularly, the preparation methods of the present disclosure are simple and the crystalline forms have low hygroscopicity, uniform particle size distribution and excellent stability, which provides new and better choices for preparation of drug containing compound (I) and is of great significance for future drug development.

SUMMARY

According to the disadvantages of the prior art, the main objective of the present disclosure is to provide novel crystalline forms of compound (I), processes for preparation and use thereof.

According to the objective of the present disclosure, crystalline form CS3 of compound (I) is provided (hereinafter referred to as Form CS3), Form CS3 is an anhydrate.

The X-ray powder diffraction pattern of Form CS3 shows characteristic peaks at 2theta values of 20.5°±0.2°, 15.4°±0.2° and 22.3°±0.2° using CuKα radiation.

Furthermore, the X-ray powder diffraction pattern of Form CS3 shows one or two or three characteristic peaks at 2theta values of 7.8°±0.2°, 17.0°±0.2°, 17.9°±0.2°. Preferably, the X-ray powder diffraction pattern of Form CS3 shows three characteristic peaks at 2theta values of 7.8°±0.2°, 17.0°±0.2°, 17.9°±0.2°.

Furthermore, the X-ray powder diffraction pattern of Form CS3 shows one or two or three characteristic peaks at 2theta values of 8.4°±0.2°, 5.1°±0.2° and 19.1°±0.2°. Preferably, the X-ray powder diffraction pattern of Form CS3 shows three characteristic peaks at 2theta values of 8.4°±0.2°, 5.1°±0.2° and 19.1°±0.2°.

Without any limitation being implied, the X-ray powder diffraction pattern of Form CS3 shows one or two or three or four or five or six or seven or eight or nine characteristic peaks at 2theta values of 20.5°±0.2°, 15.4°±0.2°, 22.3°±0.2°, 7.8°±0.2°, 17.0°±0.2°, 17.9°±0.2°, 8.4°±0.2°, 5.1°±0.2°, 19.1°±0.2° using CuKα radiation.

Without any limitation being implied, in a specific embodiment, the X-ray powder diffraction pattern of Form CS3 is substantially as depicted in FIG. 1A.

According to the objective of the present disclosure, a process for preparing Form CS3 is also provided, wherein the process comprises:

1) Suspending solid of compound (I) into a solvent mixture comprising alcohols and water or alcohols and esters, then, stirring the solution at 0-80° C. to obtain Form CS3. Preferably, said mixture of alcohols and water is a mixture of isopropanol and water, said mixture of alcohols and esters is a mixture of isopropanol and isopropyl acetate; or 2) Adding solid of compound (I) into a solvent to obtain a solution of compound (I), and adding an anti-solvent slowly into the solution of compound (I), wherein the solvent is halogenated hydrocarbons, and the anti-solvent is aromatic hydrocarbons; Or adding the solution of compound (I) into an anti-solvent, wherein the solvent is ethers, and the anti-solvent is alkanes, stirring at room temperature to obtain Form CS3.

Preferably, said halogenated hydrocarbon is chloroform, said aromatic hydrocarbon is toluene, said ether is tetrahydrofuran or 2-methyltetrahydrofuran, said alkane is n-heptane.

Form CS3 of the present disclosure has at least one of the following advantages:

1) Compared with prior art, Form CS3 of the present disclosure is almost non hygroscopic. The weight gain of the solid of prior art at 80% RH is 2.44%, and the solid of prior art has high hygroscopicity. The weight gain of Form CS3 of the present disclosure at 80% RH is 0.15%. Due to the low hygroscopicity, weight change and uncertainty of drug substance content caused by water absorption can be avoided, which is beneficial to long-term storage of drug and reduces the cost of material storage and quality control. Due to the low hygroscopicity, instability during drug preparation and/or storage and the un-processability of formulation caused by external factors such as environmental moisture can be avoided. Low hygroscopicity is advantageous for accurate quantification and later transportation and storage of the drug.

2) Compared with prior art, Form CS3 of the present disclosure has suitable and uniform particle size distribution. The average particle size of Form CS3 is smaller than 400 μm. Preferably, the average particle size of Form CS3 is smaller than 200 μm. Preferably, the average particle size of Form CS3 is smaller than 100 μm. In a specific embodiment, the average particle size of Form CS3 is 26.3 μm, D90 (the size in microns below which 90 percent of the particles reside on a volume basis) is 62.8 μm. The average particle size of prior art is 452.5 μm and D90 is 870.3 μm. Compared with prior art, Form CS3 has a smaller particle size, which increases the specific surface area of the drug substance, improves the dissolution rate of drug, thereby facilitating drug absorption and further improving the bioavailability of the drug. Moreover, compared with prior art, Form CS3 has a narrower particle size distribution and a monodisperse normal distribution, indicating that the powder of Form CS3 is highly homogeneous. API with uniform particle size distribution can be used in the formulation process directly, which avoids the complex pretreatment process, simplifies the production process, reduces cost, improves the uniformity of drug products, and makes the quality of pharmaceutical preparations more controllable.

3) Form CS3 of the present disclosure has good stability. The crystalline form of Form CS3 doesn't change for at least 3 weeks when stored in open dishes under the condition of 25° C./60% RH, 40° C./75% RH and/or 60° C./75% RH. Preferably, doesn't change for at least 6 months. Preferably, doesn't change for at least 1 year. Form CS3 has excellent stability, which can ensure that the quality of the drug will not be affected as polymorphic transition will not occur in the process of preparation, transportation and storage. It is of great significance to ensure the efficacy and safety of the drug and prevent the occurrence of adverse drug reactions.

According to the objective of the present disclosure, crystalline form CS2 of Compound (I) is provided (hereinafter referred to as Form CS2).

The X-ray powder diffraction pattern of Form CS2 shows characteristic peaks at 2theta values of 20.5°±0.2°, 16.8°±0.2°, 4.3°±0.2° using CuKα radiation.

Furthermore, the X-ray powder diffraction pattern of Form CS2 shows one or two or three characteristic peaks at 2theta values of 8.4°±0.2°, 17.6°±0.2°, 14.9°±0.2°. Preferably, the X-ray powder diffraction pattern of Form CS2 shows three characteristic peaks at 2theta values of 8.4°±0.2°, 17.6°±0.2°, 14.9°±0.2°.

Without any limitation being implied, the X-ray powder diffraction pattern of Form CS2 shows one or two or three or four or five or six characteristic peaks at 2theta values of 20.5°±0.2°, 16.8°±0.2°, 4.3°±0.2°, 8.4°±0.2°, 17.6°±0.2°, 14.9°±0.2° using CuKα radiation. Without any limitation being implied, in a specific embodiment, the X-ray powder diffraction pattern of Form CS2 is substantially as depicted in FIG. 2A. Without any limitation being implied, Form CS2 has isomorphism.

According to the objective of the present disclosure, a process for preparing Form CS2 is also provided. Wherein the process comprises:

1) Mixing solid of compound (I) with methanol or a solvent mixture of ethanol and acetone, filtering after dissolved, storing the filtrate in a larger sealed device containing acetonitrile at 0-30° C. to obtain Form CS2; or 2) Suspending solid of compound (I) into acetonitrile, then stirring the solution at 0-30° C. to obtain Form CS2.

Form CS2 of the present disclosure has at least one of the following advantages:

1) Compared with prior art, Form CS2 of the present disclosure has lower hygroscopicity. The weight gain of the solid of prior art under 80% RH is 2.44%, and the solid of prior art has high hygroscopicity. The weight gain of Form CS2 of the present disclosure at 80% RH is 0.46%. Due to the low hygroscopicity, weight change and uncertainty of drug substance content caused by water absorption can be avoided, which is beneficial to long-term storage of drug and reduces the cost of material storage and quality control. Due to the low hygroscopicity, instability during drug preparation and/or storage and the un-processability of formulation caused by external factors such as environmental moisture can be avoided. Low hygroscopicity is advantageous for accurate quantification and later transportation and storage of the drug.

2) Compared with prior art, Form CS2 of the present disclosure has suitable particle size and good uniformity. Average particle size of Form CS2 is less than 400 μm. Preferably, the average particle size of Form CS2 is less than 200 μm. Preferably, the average particle size of Form CS2 is less than 100 μm. In a specific embodiment, the average particle size of Form CS2 is 41.9 μm, D90 (the size in microns below which 90 percent of the particles reside on a volume basis) is 87.5 μm, but the average particle size of prior art is 452.5 μm, D90 is 870.3 μm. Compared with prior art, Form CS2 has a smaller crystal size, which can increase the specific surface area of drugs, improve the dissolution rate of drugs, facilitate drug absorption, and thus improving bioavailability. Moreover, compared with prior art, Form CS2 has a narrower particle size distribution and a monodisperse normal distribution, indicating that the powder of Form CS2 is highly homogeneous. API with uniform particle size distribution can be directly applied in the preparation process, which avoiding the complex pretreatment process of API, simplifying the process, reducing the production cost, improving the uniformity of pharmaceutical preparations, and making the quality of pharmaceutical preparations more controllable.

3) Form CS2 of the present disclosure has good stability. The Form CS2 doesn't change for at least 3 weeks when stored in open dishes under the condition of 25° C./60% RH or 40° C./75% RH or 60° C./75% RH. Preferably, doesn't change for at least 3 months. Preferably, doesn't change for at least 6 months. Preferably, doesn't change for at least 1 year. Form CS2 has excellent stability, which can ensure that the quality of the drug will not be affected as polymorphic transition will not occur in the process of preparation, transportation and storage. It is of great significance to ensure the efficacy and safety of the drug and prevent the occurrence of adverse drug reactions.

According to the objective of the present disclosure, crystalline form CS5 of Compound (I) is provided (hereinafter referred to as Form CS5).

The X-ray powder diffraction pattern of Form CS5 shows characteristic peaks at 2theta values of 4.8°±0.2°, 9.7°±0.2°, 6.4°±0.2° using CuKα radiation.

Furthermore, the X-ray powder diffraction pattern of Form CS5 shows one or two or three or four characteristic peaks at 2theta values of 20.9°±0.2°, 16.8°±0.2°, 23.3°±0.2°, 14.6°±0.2°. Preferably, the X-ray powder diffraction pattern of Form CS5 shows three characteristic peaks at 2theta values of 20.9°±0.2°, 16.8°±0.2°, 23.3°±0.2°, 14.6°±0.2°.

Without any limitation being implied, the X-ray powder diffraction pattern of Form CS5 shows one or two or three or four or five or six or seven characteristic peaks at 2theta values of 4.8°±0.2°, 9.7°±0.2°, 6.4°±0.2°, 20.9°±0.2°, 16.8°±0.2°, 23.3°±0.2°, 14.6°±0.2° using CuKα radiation.

Without any limitation being implied, in a specific embodiment of the present disclosure, Form CS5 is a hydrate, and the X-ray powder diffraction pattern of Form CS5 is substantially as depicted in FIG. 3A.

According to the objective of the present disclosure, a process for preparing Form CS5 is also provided. The process comprises: Adding solid of compound (I) into a solvent selected from alcohols to obtain a solution of compound (I), and adding acetonitrile slowly into the solution of compound (I), stirring at room temperature until solid precipitates, then, separating and drying to obtain Form CS5. Preferably, said alcohols are methanol, ethanol and isopropanol.

Form CS5 of the present disclosure has at least one of the following advantages:

1) Compared with prior art, Form CS5 of the present disclosure has lower hygroscopicity. Weight gain of solid of prior art under 80% RH is 2.44%, and the hygroscopicity is high. The weight gain of Form CS5 of the present disclosure at 80% RH is 0.35%. Due to the low hygroscopicity, weight change and uncertainty of drug substance content caused by water absorption can be avoided, which is beneficial to long-term storage of drug and reduces the cost of material storage and quality control. Due to the low hygroscopicity, instability during drug preparation and/or storage and the un-processability of formulation caused by external factors such as environmental moisture can be avoided. Low hygroscopicity is advantageous for accurate quantification and later transportation and storage of the drug.

2) Compared with prior art, Form CS5 of the present disclosure has suitable particle size and good uniformity. Average particle size of Form CS5 is less than 400 μm. Preferably, the average particle size of Form CS5 is less than 200 μm. Preferably, the average particle size of Form CS5 is less than 100 μm. In a specific embodiment, the average particle size of Form CS5 is 75.6 μm, but the average particle size of prior art is 452.5 μm. Compared with prior art, Form CS5 has a smaller crystal size, which can increase the specific surface area of drugs, improve the dissolution rate of drugs, facilitate drug absorption, and thus improving bioavailability. Moreover, compared with prior art, Form CS5 has a narrower particle size distribution and a monodisperse normal distribution, indicating that the powder of Form CS5 is highly homogeneous. API with uniform particle size distribution can be directly applied in the preparation process, which avoiding the complex pretreatment process of API, simplifying the process, reducing the production cost, improving the uniformity of pharmaceutical preparations, and making the quality of pharmaceutical preparations more controllable.

3) Form CS5 of the present disclosure has good stability. The Form CS5 doesn't change for at least 3 weeks when stored in open dishes under the condition of 25° C./60% RH or 40° C./75% RH or 60° C./75% RH. Preferably, doesn't change for at least 3 months. Preferably, doesn't change for at least 6 months. Preferably, doesn't change for at least 1 year. Form CS5 has excellent stability, which can ensure that the quality of the drug will not be affected as polymorphic transition will not occur in the process of preparation, transportation and storage. It is of great significance to ensure the efficacy and safety of the drug and prevent the occurrence of adverse drug reactions.

According to the objective of the present disclosure, crystalline form CS8 of Compound (I) is provided (hereinafter referred to as Form CS8).

The X-ray powder diffraction pattern of Form CS8 shows characteristic peaks at 2theta values of 6.0°±0.2°, 15.5°±0.2°, 20.7°±0.2° using CuKα radiation.

Furthermore, the X-ray powder diffraction pattern of Form CS8 shows one or two or three or four characteristic peaks at 2theta values of 21.8°±0.2°, 9.1°±0.2°, 19.9°±0.2°, 22.9°±0.2°. Preferably, the X-ray powder diffraction pattern of Form CS8 shows four characteristic peaks at 2theta values of 21.8°±0.2°, 9.1°±0.2°, 19.9°±0.2°, 22.9°±0.2°.

Without any limitation being implied, the X-ray powder diffraction pattern of Form CS8 shows one or two or three or four or five or six or seven characteristic peaks at 2theta values of 6.0°±0.2°, 15.5°±0.2°, 20.7°±0.2°, 21.8°±0.2°, 9.1°±0.2°, 19.9°±0.2°, 22.9°±0.2° using CuKα radiation.

Without any limitation being implied, in a specific embodiment of the present disclosure, the X-ray powder diffraction pattern of Form CS8 is substantially as depicted in FIG. 4A.

According to the objective of the present disclosure, a process for preparing Form CS8 is also provided. The process comprises:

Storing Form CS2 at room temperature for 7-30 days, heating the obtained sample to 95° C. ±2° C. at a rate of 5-20° C./min with nitrogen purging, holding at 95° C. ±2° C. for 1-10 min, and then cooling to room temperature at a rate of 5-20° C./min to obtain Form CS8.

Form CS8 of the present disclosure has at least one of the following advantages:

1) Compared with prior art, Form CS8 of the present disclosure has lower a lower hygroscopicity. Weight gain of solid of prior art under 80% RH is 2.44%, and the hygroscopicity is high. The weight gain of Form CS8 of the present disclosure at 80% RH is 0.40%. Due to the low hygroscopicity, weight change and uncertainty of drug substance content caused by water absorption can be avoided, which is beneficial to long-term storage of drug and reduces the cost of material storage and quality control. Due to the low hygroscopicity, instability during drug preparation and/or storage and the un-processability of formulation caused by external factors such as environmental moisture can be avoided. Low hygroscopicity is advantageous for accurate quantification and later transportation and storage of the drug.

2) Compared with prior art, Form CS8 of the present disclosure has suitable particle size, and has good uniformity. Average particle size of Form CS8 is less than 400 µm. Preferably, the average particle size of Form CS8 is less than 200 µm. Preferably, the average particle size of Form CS8 is less than 100 µm. Form CS8 has a smaller crystal size, which can increase the specific surface area of drugs, improve the dissolution rate of drugs, facilitate drug absorption, and thus improving bioavailability. Moreover, compared with prior art, Form CS8 has a narrower particle size distribution and a monodisperse normal distribution, indicating that the powder of Form CS8 is highly homogeneous. API with uniform particle size distribution can be directly applied in the preparation process, which avoiding the complex pretreatment process of API, simplifying the process, reducing the production cost, improving the uniformity of pharmaceutical preparations, and making the quality of pharmaceutical preparations more controllable.

3) Form CS8 of the present disclosure has good stability. The Form CS8 doesn't change for at least 3 weeks when stored in open dishes under the condition of 25° C./60% RH or 40° C./75% RH or 60° C./75% RH. Preferably, doesn't change for at least 3 months. Preferably, doesn't change for at least 6 months. Preferably, doesn't change for at least 1 year. Form CS8 has good stability, and it is of great significance to ensure the efficacy and safety of drugs and prevent the occurrence of adverse drug reactions.

In processes for preparing crystalline forms of the present disclosure:

Said "room temperature" is 25° C. ±5° C.

Said "stirring" is accomplished by using a conventional method in the field such as magnetic stirring or mechanical stirring and the stirring speed is 50 to 1800 r/min, preferably the magnetic stirring speed is 300 to 900 r/min and mechanical stirring speed is 100 to 300 r/min.

Said "separation" is accomplished by using a conventional method in the field such as centrifugation or filtration. The operation of "centrifugation" is as follows: the sample to be separated is placed into the centrifuge tube, and then centrifuged at a rate of 10000 r/min until the solid all sink to the bottom of the tube.

Said "drying" is accomplished at room temperature or a higher temperature. The drying temperature is from room temperature to about 60° C., or to 50° C., or to 40° C. The drying time can be 2 to 48 hours, or overnight. Drying is accomplished in a fume hood, oven or vacuum oven.

Said "evaporating" is accomplished by using a conventional method in the field such as slow evaporation or rapid evaporation. For example, evaporation is accomplished in a container covered by sealing film with pinholes.

Said "cooling" is accomplished by using conventional methods in the field such as slow cooling and rapid cooling. Slow cooling is usually accomplished at the speed of 0.1° C./min. Isomorphous crystals are formed during the crystallization process, when molecules in some positions are partially or completely replaced by other molecules with similar properties. The obtained isomorphous crystals are single phase crystals. Isomorphism doesn't change the crystal structure or connectivity of the crystal. There may be slight changes in unit cell parameters. As a result, the XRPD patterns of isomorphous crystals are identical or similar.

In the present disclosure, "crystal" or "crystalline form" refers to the crystal or the crystalline form being identified by the X-ray diffraction pattern shown herein. Those skilled in the art are able to understand that physicochemical properties discussed herein can be characterized. The experimental errors depend on the instrument conditions, the sampling processes and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. In addition, the experimental error of the diffraction peak position is usually 5% or less, and the error of these positions should also be taken into account. An error of ±0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have exactly the same X-ray diffraction pattern of the example shown herein. As used herein, "the same XRPD pattern" does not mean absolutely the same, the same peak positions may differ by ±0.2° and the peak intensity allows for some variability. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, crystalline Form CS2, CS3, CS5, CS8 of the present disclosure is pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

It should be noted that the number and the number range should not be understood as the number or number range themselves only. It should be understood by those skilled in the art that the specific number can be shifted at specific technical environment without departing from the spirit and principle of the present disclosure. In the present disclosure, the number of shift ranges expected by one of skilled in the art is represented by the term "about".

In addition, the present disclosure provides a pharmaceutical composition, said pharmaceutical composition comprises a therapeutically and/or prophylactically effective amount of Form CS2, CS3, CS5 or CS8 and pharmaceutically acceptable carriers, diluents or excipients.

Furthermore, Form CS2, CS3, CS5 or CS8 can be used for preparing drugs treating non-alcoholic steatohepatitis, gallstones, cholesterol gallstone and atherosclerosis.

DETAILED DESCRIPTION

Figure 1A:
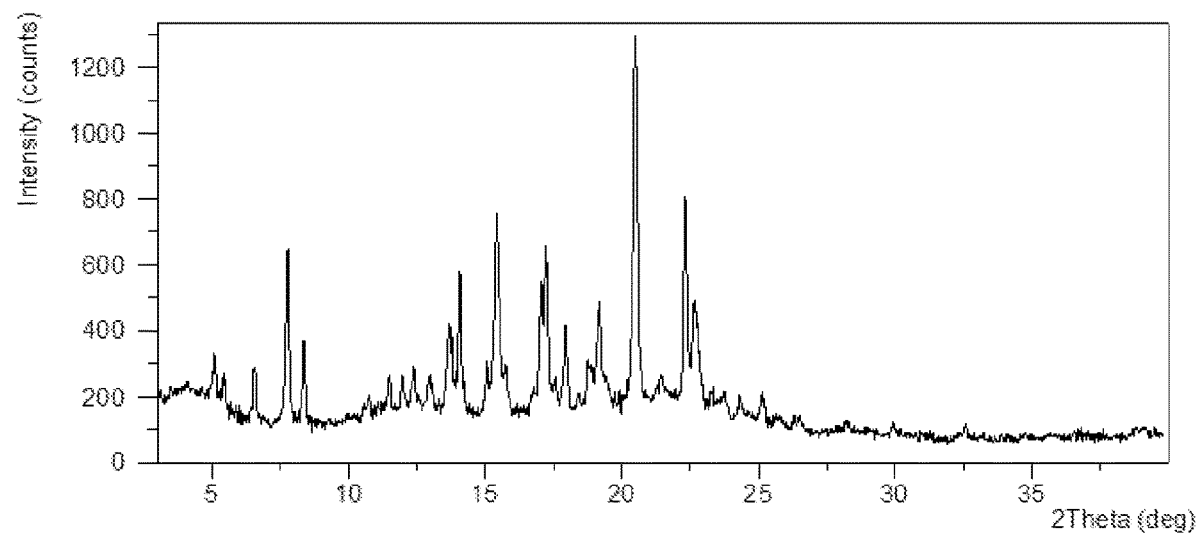
FIG. 1A shows an XRPD pattern of Form CS3 of the present disclosure.

The present disclosure is further illustrated by the following examples which describe the preparation and use of the crystalline forms of the present disclosure in detail. It is obvious to those skilled in the art that many changes in the materials and methods can be accomplished without departing from the scope of the present disclosure.

The abbreviations used in the present disclosure are explained as follows:
XRPD: X-ray Powder Diffraction
DSC: Differential Scanning calorimetry
TGA: Thermal Gravimetric Analysis
DVS: Dynamic Vapor Sorption
$^1$H NMR: Proton Nuclear Magnetic Resonance
PSD: Particle Size Distribution X-ray powder diffraction patterns in the present disclosure were acquired by a Bruker D2 PHASER X-ray powder diffractometer. The parameters of the X-ray powder diffraction method of the present disclosure are as follows:

X-ray Reflection: Cu, Kα

Kα1 (Å): 1.54060; Kα2 (Å): 1.54439

Kα2/Kα1 intensity ratio: 0.50

Voltage: 30 (kV)

Current: 10 (mA)

Scan range: from 3.0 degree to 40.0 degree

Differential scanning calorimetry (DSC) data in the present disclosure were acquired by a TA Q2000. The parameters of the DSC method of the present disclosure are as follows:

Heating rate: 10° C./min

Purge gas: nitrogen

Thermal gravimetric analysis (TGA) data in the present disclosure were acquired by a TA Q500. The parameters of the TGA method of the present disclosure are as follows:

Heating rate: 10° C./min

Purge gas: nitrogen

Proton nuclear magnetic resonance spectrum data ($^1$H NMR) were collected from a Bruker Avance II DMX 400M HZ NMR spectrometer. 1-5 mg of sample was weighed and dissolved in 0.5 mL of deuterated dimethyl sulfoxide to obtain a solution with a concentration of 2-10 mg/mL.

The particle size distribution data in the present disclosure were acquired by an S3500 laser particle size analyzer of Microtrac. Microtrac S3500 is equipped with an SDC (Sample Delivery Controller). The test was carried out in wet mode, and the dispersion medium is Isopar G. The parameters are as follows:

| | |
|---|---|
| Size distribution: Volume | Run Time: 10 s |
| Dispersion medium: Isopar G | Particle coordinates: Standard |
| Run Number: 3 | Fluid refractive index: 1.42 |
| Particle Transparency: Trans | Residuals: Enabled |
| Particle refractive index: 1.5 | Flow rate: 60%* |
| Particle shape: Irregular | Filtration: Enabled |
| Ultrasonication power: 30 W | Ultrasonication time: 30 s |

*Flow rate 60% is 60% of 65 mL/s.

Unless otherwise specified, the following examples were conducted at room temperature. Solid of compound (I) used in the following examples were prepared by known methods in the prior art, the method disclosed in CN100386339C.

Example 1

Preparation of Form CS3 Example 1

As shown in Table 1A, certain amount of compound (I) was weighed into each of three glass vials followed by adding corresponding volume of solvent to form a suspension. These suspensions were stirred at RT, then centrifuged and dried. The obtained solid was collected and labeled as sample 1-a, 1-b, 1-c.

TABLE 1A

| Sample ID | Mass (mg) | Solvent (v/v) | Volume (mL) |
|---|---|---|---|
| 1-a | 10.6 | IPA/H$_2$O 1:1 | 0.4 |
| 1-b | 10.4 | EtOH/EtOAc 1:9 | 0.5 |
| 1-c | 9.1 | IPA/IPAc 1:1 | 0.4 |

Sample 1-a, 1-b, 1-c were confirmed to be Form CS3 by XRPD. The XRPD pattern of sample 1-a is depicted in FIG. 1A, and the XRPD data are listed in Table 1B. The XRPD patterns of sample 1-b and 1-c are the same as or similar to that of sample 1-a.

TABLE 1B

| 2θ | d spacing | Intensity % |
|---|---|---|
| 5.10 | 17.31 | 21.16 |
| 5.44 | 16.24 | 16.26 |
| 6.56 | 13.47 | 17.60 |
| 7.76 | 11.40 | 47.21 |
| 8.40 | 10.52 | 23.60 |
| 10.76 | 8.22 | 11.09 |
| 11.50 | 7.70 | 16.24 |
| 11.98 | 7.39 | 16.03 |
| 12.39 | 7.14 | 15.35 |
| 12.98 | 6.82 | 16.15 |
| 13.69 | 6.47 | 28.31 |
| 14.08 | 6.29 | 41.22 |
| 15.07 | 5.88 | 19.39 |
| 15.41 | 5.75 | 54.37 |
| 15.75 | 5.63 | 18.98 |

TABLE 1B-continued

| 2θ | d spacing | Intensity % |
|---|---|---|
| 16.72 | 5.30 | 11.17 |
| 17.04 | 5.20 | 39.33 |
| 17.21 | 5.15 | 48.52 |
| 17.56 | 5.05 | 15.91 |
| 17.94 | 4.94 | 28.29 |
| 18.42 | 4.82 | 11.18 |
| 18.76 | 4.73 | 20.05 |
| 19.17 | 4.63 | 32.94 |
| 20.49 | 4.33 | 100.00 |
| 21.44 | 4.14 | 15.85 |
| 22.32 | 3.98 | 60.51 |
| 22.67 | 3.92 | 34.67 |
| 23.28 | 3.82 | 11.51 |
| 23.73 | 3.75 | 11.35 |
| 24.33 | 3.66 | 10.58 |
| 25.14 | 3.54 | 10.29 |
| 25.70 | 3.47 | 5.16 |
| 26.49 | 3.36 | 5.65 |

Figure 1B:
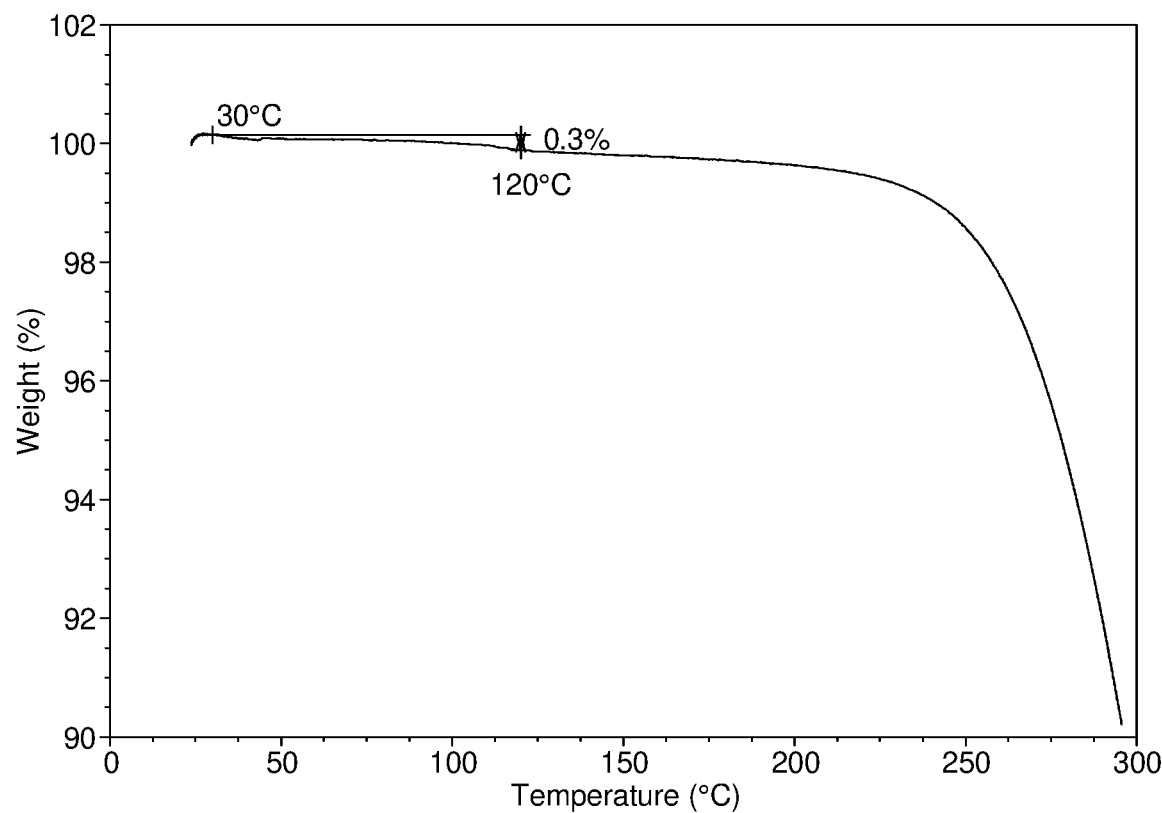
FIG. 1B shows a TGA curve of Form CS3 of the present disclosure.

The TGA curve of Form CS3 shows about 0.3% weight loss when heated to 120° C., which is depicted in FIG. 1B.

Figure 1C:
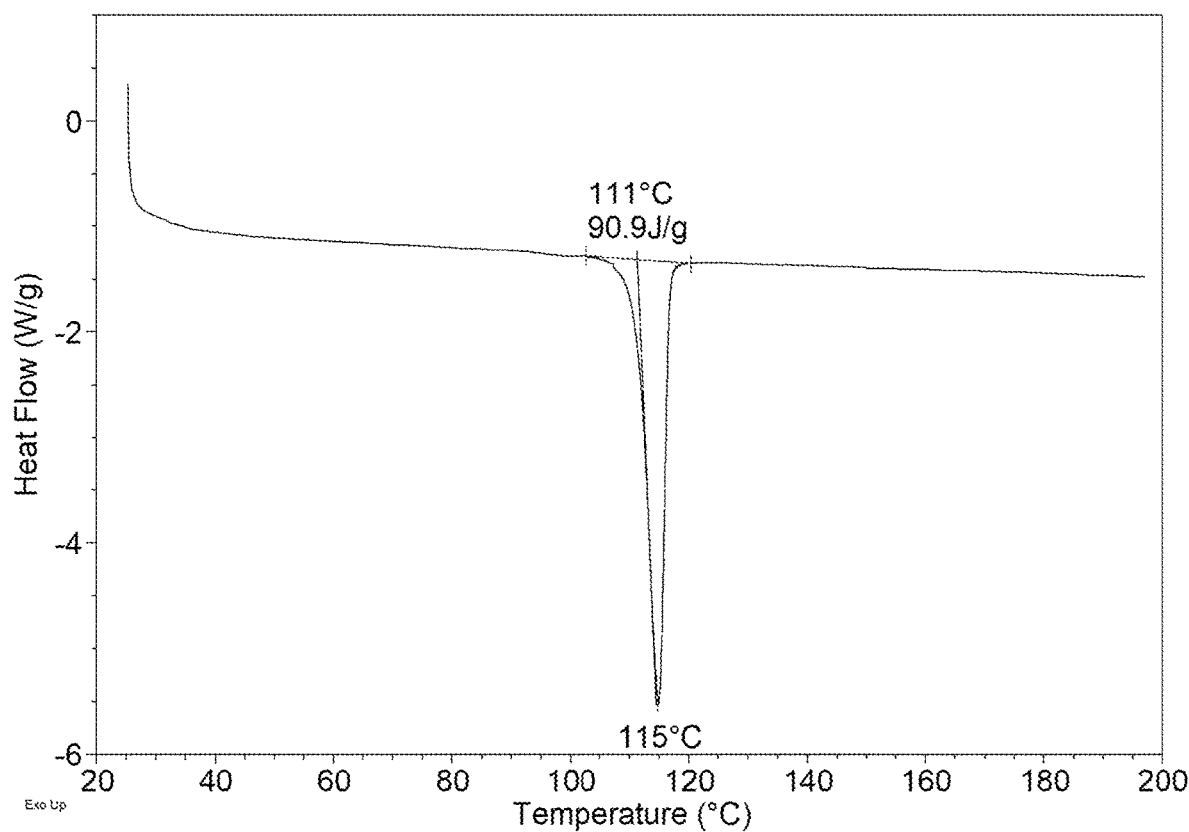
FIG. 1C shows a DSC curve of Form CS3 of the present disclosure.

The DSC curve of Form CS3 is depicted in FIG. 1C, which shows one endothermic peak at around 111° C. (onset temperature).

Figure 1D:
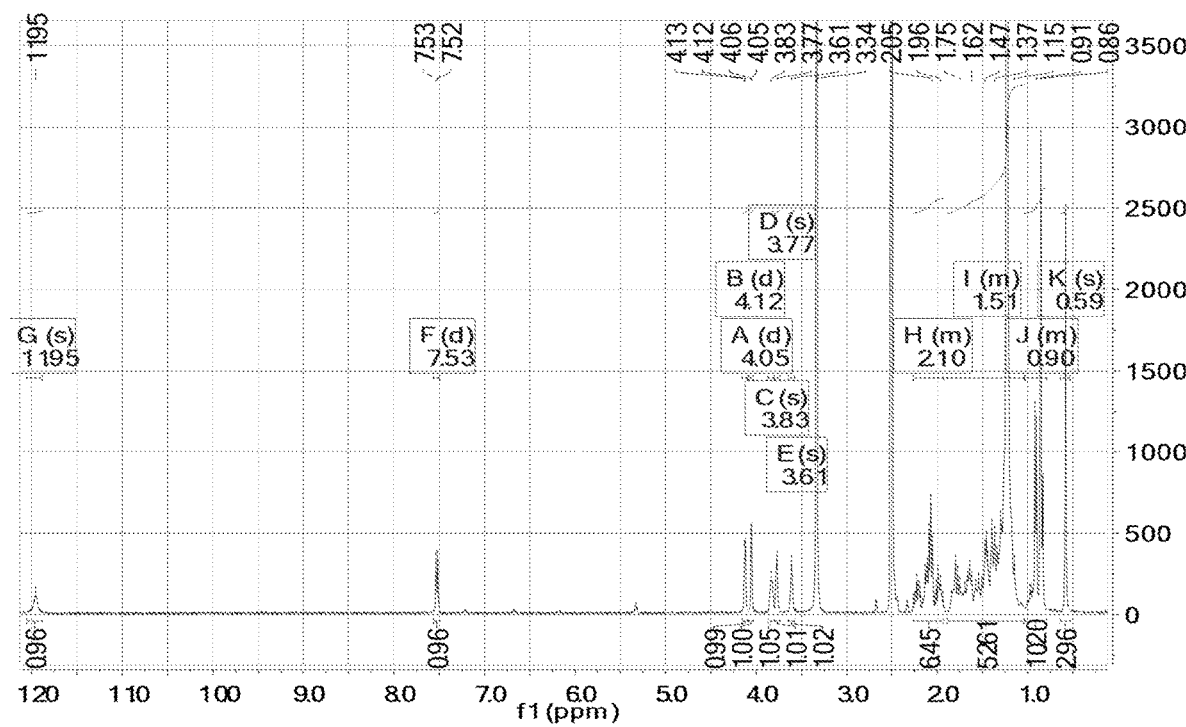
FIG. 1D shows a $^1$H NMR spectrum of Form CS3 of the present disclosure.

The $^1$H NMR spectrum of Form CS3 is depicted in FIG. 1D, and the corresponding data are: $^1$H NMR (400 MHz, DMSO) δ 11.95 (s, 1H), 7.53 (d, J=7.0 Hz, 1H), 4.12 (d, J=3.3 Hz, 1H), 4.05 (d, J=3.2 Hz, 1H), 3.83 (s, 1H), 3.77 (s, 1H), 3.61 (s, 1H), 2.26-1.93 (m, 6H), 1.89-1.03 (m, 53H), 1.04-0.79 (m, 10H), 0.59 (s, 3H). Except water, no other solvent residue was observed.

Preparation of Form CS3 Example 2:

15.6 mg of compound (I) was dissolved into 0.5 mL of CHCl$_3$. The solution was filtered and 2.0 mL of toluene was added into the filtrate. Then the clear solution was stirred until solid crystallized. The solid was collected by centrifugation, and the obtained solid was dried and labeled as sample 1-d. Sample 1-d was confirmed to be Form CS3.

Preparation of Form CS3 Example 3:

As shown in Table 1C, certain amount of compound (I) was dissolved in corresponding volume of solvent. After filtering, the filtrate was added into certain volume of anti-solvent. The suspension was stirred at RT until a large amount of solid precipitated. The solid was collected by centrifugation, and the obtained solid was dried and labeled as sample 1-e and 1-f. Sample 1-e and 1-f were confirmed to be Form CS3.

TABLE 1C

| Sample ID | Method | Mass (mg) | Solvent | Solvent Volume (mL) | Volume of filtrate (mL) | Anti-solvent | Volume of anti-solvent (mL) |
|---|---|---|---|---|---|---|---|
| 1-e | Reverse anti-solvent addition | 15.6 | THF | 0.5 | 0.2 | n-Heptane | 2.0 |
| 1-f | Reverse anti-solvent addition | 15.4 | 2-MeTHF | 1.0 | 0.4 | n-Heptane | 2.0 |

Stability Study of Form CS3

As active pharmaceutical ingredient plays an important part in drug products, it is vital that the crystalline active pharmaceutical ingredient has good physical and chemical stability. Good physical stability avoids crystal transformation during the storage and formulation processes, thereby ensuring consistent and controllable quality of the drug substance and drug product.

Solid samples of Form CS3 were stored under different conditions of 25° C./60% RH and 40° C./75% RH in open dishes for one year. Crystalline form was checked by XRPD. The results are shown in Table 1D.

TABLE 1D

Figure 1E:
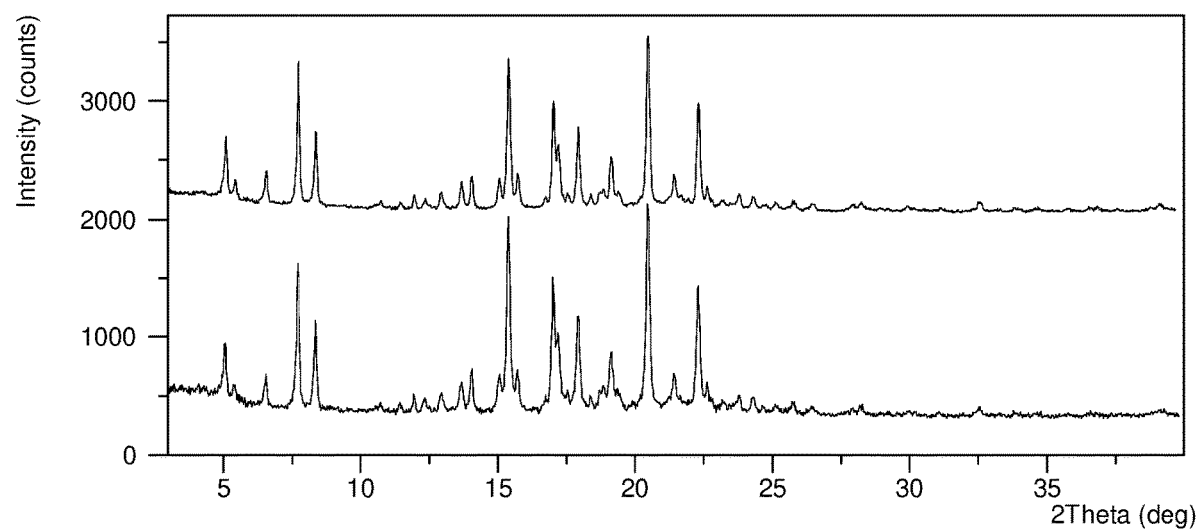
FIG. 1E shows an XRPD pattern overlay of Form CS3 of the present disclosure before and after being stored under 25° C./60% RH for one year, top: XRPD pattern before storage, bottom: XRPD pattern after storage.
Figure 1F:
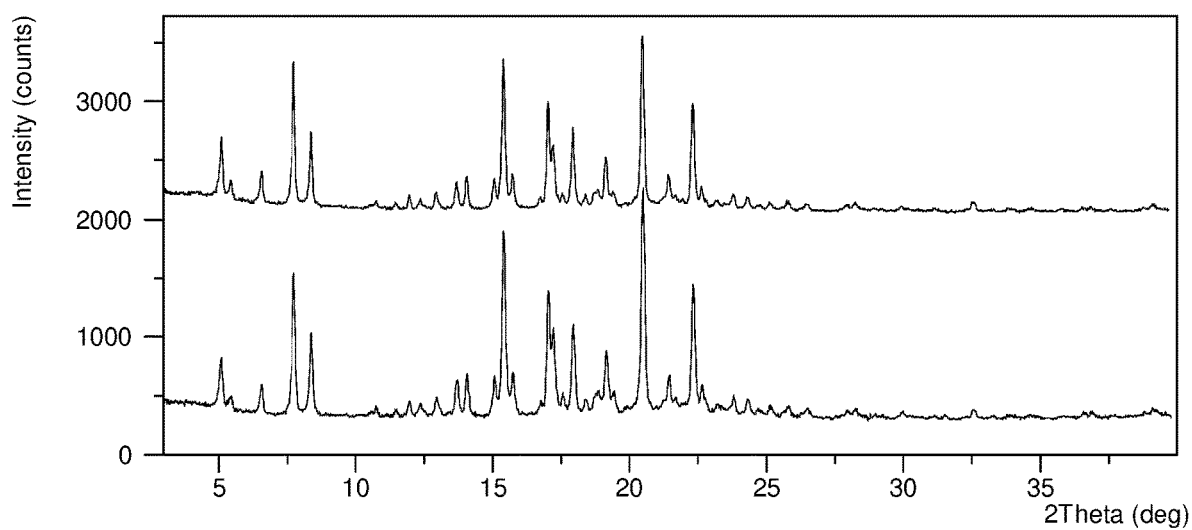
FIG. 1F shows an XRPD pattern overlay of Form CS3 of the present disclosure before and after being stored under 40° C./75% RH for one year, top: XRPD pattern before storage, bottom: XRPD pattern after storage.

| Initial crystalline form | Conditions | Time | Form change |
|---|---|---|---|
| Form CS3 (FIG. 1E top) | 25° C./60% RH | One year | No form change observed (FIG. 1E bottom) |
| Form CS3 (FIG. 1F top) | 40° C./75% RH | One year | No form change observed (FIG. 1F bottom) |

The results show that Form CS3 has good stability and meets the requirements of the guidance of stability testing of drug substances and produces of China and/or American. Therefore, Form CS3 is suitable for drug development.

Hygroscopicity Study of Form CS3

Figure 1G:
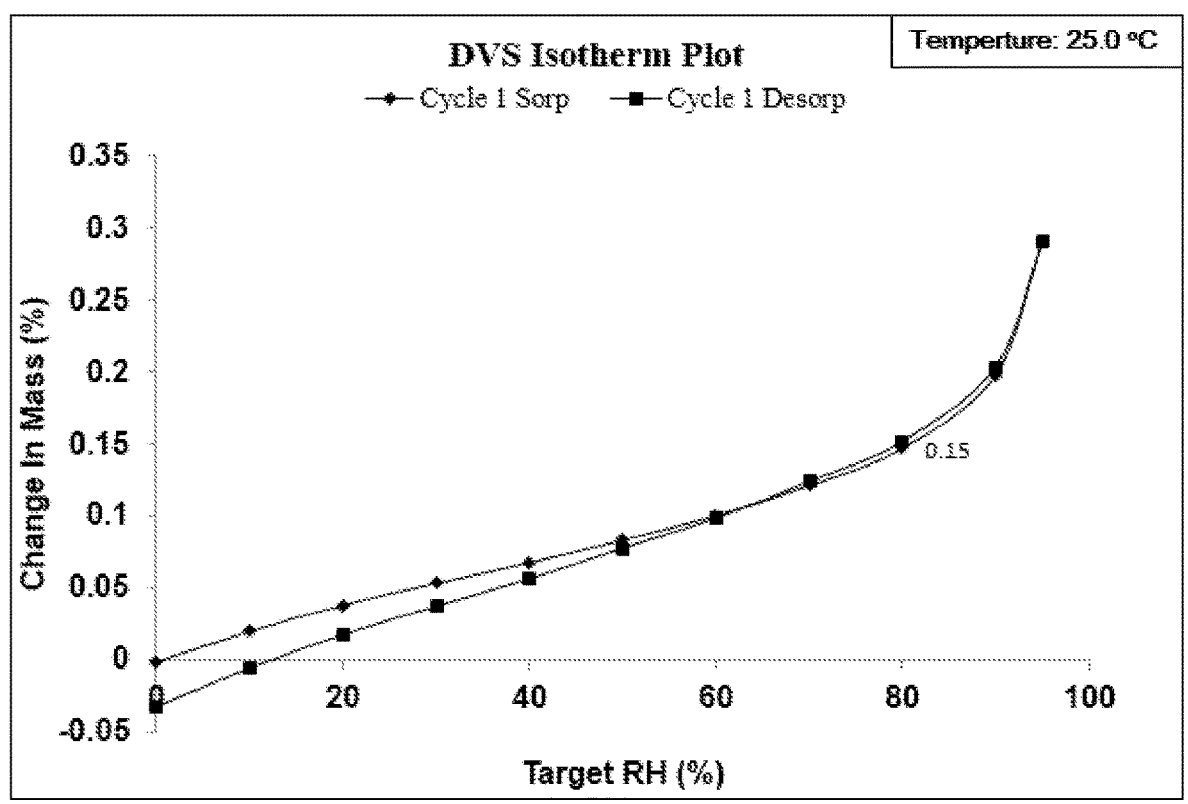
FIG. 1G shows a DVS plot of Form CS3 of the present disclosure.
Figure 1H:
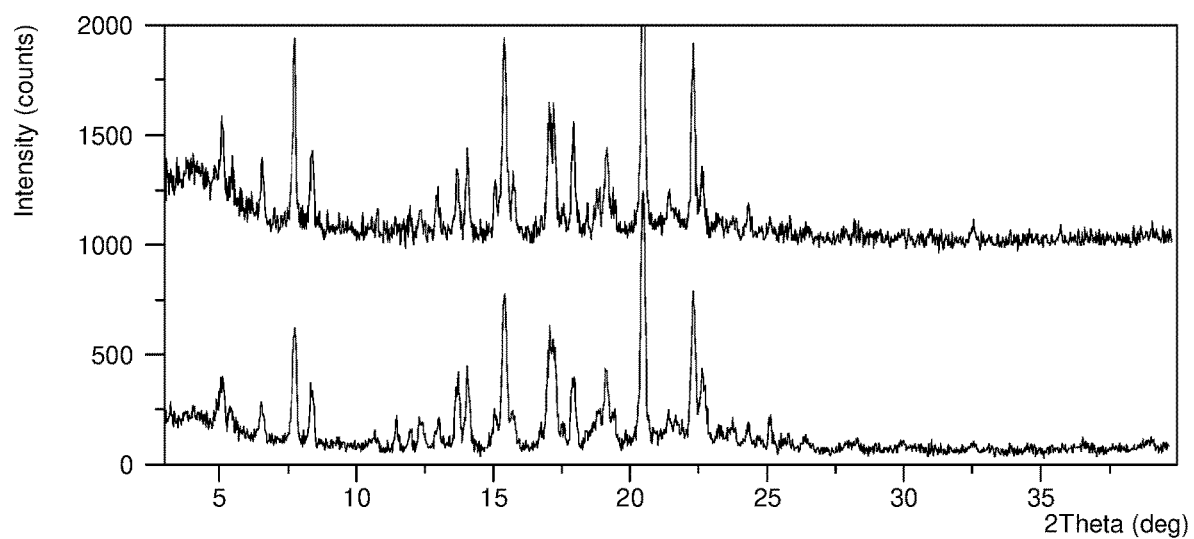
FIG. 1H shows an XRPD pattern overlay of Form CS3 of the present disclosure before and after DVS test, top: XRPD pattern before test, bottom: XRPD pattern after test.
Figure 1I:
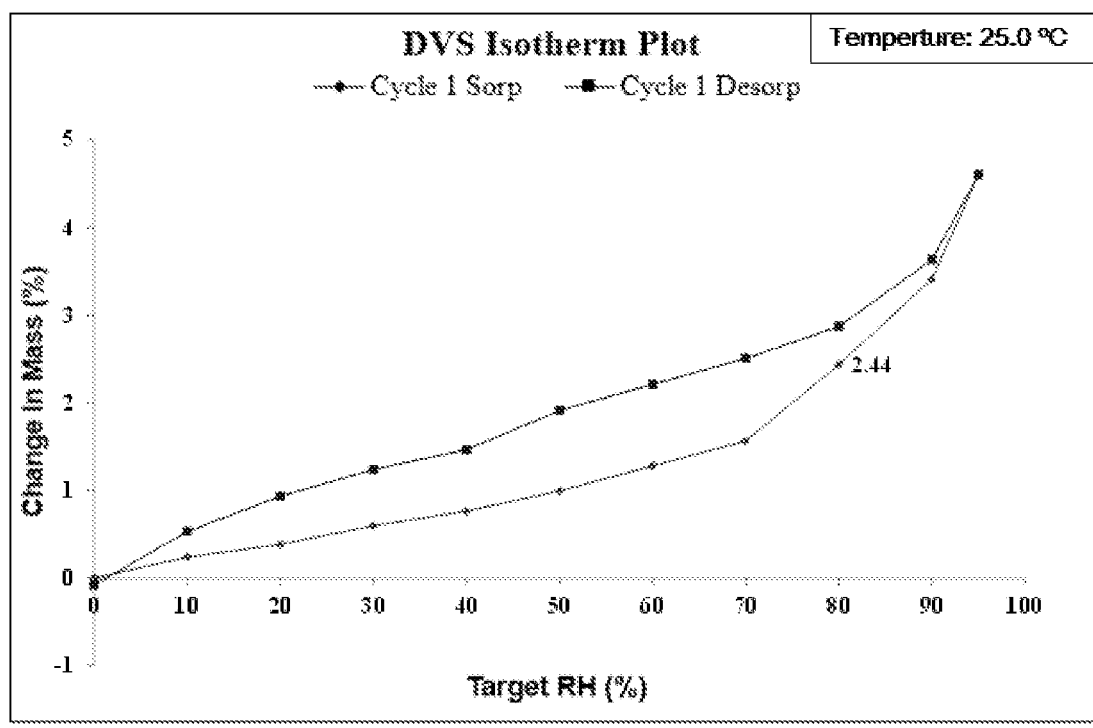
FIG. 1I shows a DVS plot of the prior art.

Dynamic vapor sorption (DVS) was applied to test hygroscopicity of Form CS3 and the solid disclosed in CN100386339C with about 15 mg of samples. The results are listed in Table 1E. As shown in FIG. 1I, the solid disclosed in prior art is hygroscopic with 2.44% weight gain under 80% RH. While Form CS3 is non hygroscopic or almost non hygroscopic with 0.15% weight gain under 80% RH. DVS plot of test hygroscopicity of Form CS3 is depicted in FIG. 1G. What's more, the crystalline form of Form CS3 didn't change after DVS test, which is depicted in FIG. 1H.

TABLE 1E

| Sample | Weight gain under 80% Relative Humidity | The definition of hygroscopicity |
|---|---|---|
| Form CS3 | 0.15% | non hygroscopic or almost non hygroscopic |
| Solid disclosed in CN100386339C | 2.44% | hygroscopic |

Description and definition of hygroscopicity (Chinese Pharmacopoeia 2015 edition appendix XIX J Drug hygroscopic test guidelines, test at 25° C. +/−1° C., 80% RH.).

deliquescent: Sufficient water is absorbed to form a liquid;
very hygroscopic: Increase in mass is equal to or greater than 15 percent;
hygroscopic: Increase in mass is less than 15 percent and equal to or greater than 2 percent;
slightly hygroscopic: Increase in mass is less than 2 percent and equal to or greater than 0.2 percent.
non hygroscopic or almost non hygroscopic: Increase in mass is less than 0.2 percent.

Particle Size Study of Form CS3

The particle size distribution of Form CS3 and the solid disclosed in CN100386339C were tested after ultrasonication for 30 seconds. The results are shown in Table 1F. The average particle size of Form CS3 is 26.3 μm, and D90 is 62.8 μm. The average particle size and D90 of the solid disclosed in prior art are 452.5 μm and 870.3 μm. Compared with prior art, Form CS3 has smaller particle size, which increases the specific surface area of the drug substance, improves the dissolution rate of drug, thereby facilitating drug absorption and further improving the bioavailability of the drug.

TABLE 1F

| Sample | MV (μm) | D10 (μm) | D50 (μm) | D90 (μm) |
|---|---|---|---|---|
| Form CS3 | 26.3 | 2.0 | 12.3 | 62.8 |
| Solid disclosed in CN100386339C | 452.5 | 95.0 | 398.8 | 870.3 |

Explanation of the abbreviations used in the present invention is as follows:

MV: Average particle diameter calculated by volume.
D10: the size in microns below which 10 percent of the particles reside on a volume basis.
D50: the size in microns below which 50 percent of the particles reside on a volume basis, also known as the median diameter.
D90: the size in microns below which 90 percent of the particles reside on a volume basis.

Figure 1J:
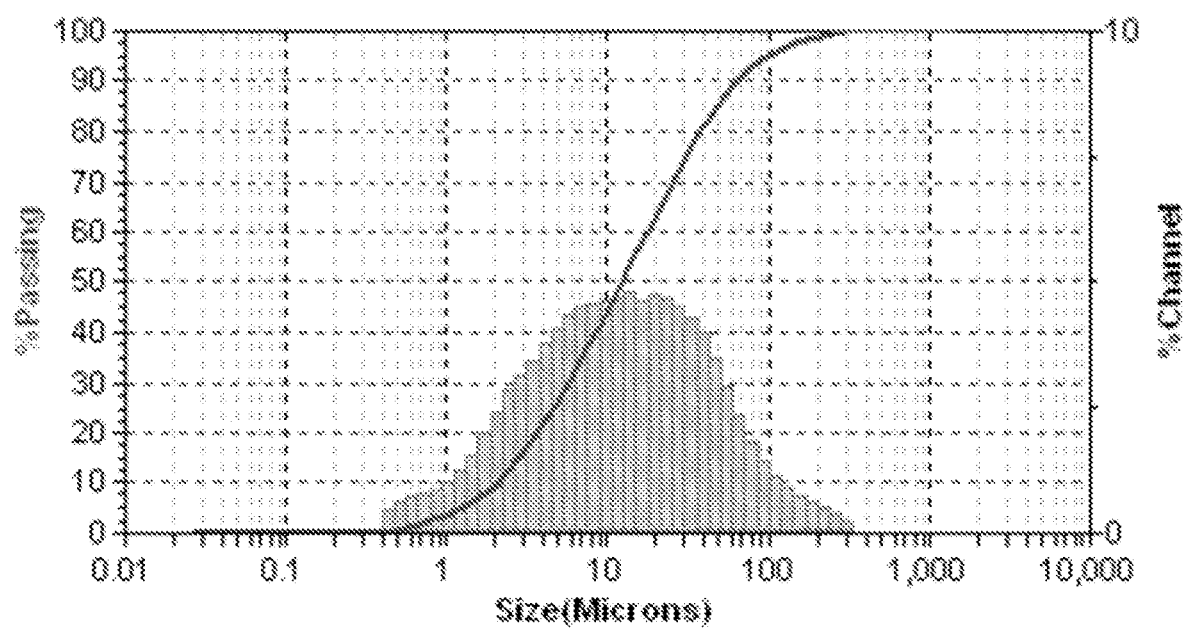
FIG. 1J shows a PSD diagram of Form CS3 of the present disclosure.
Figure 1K:
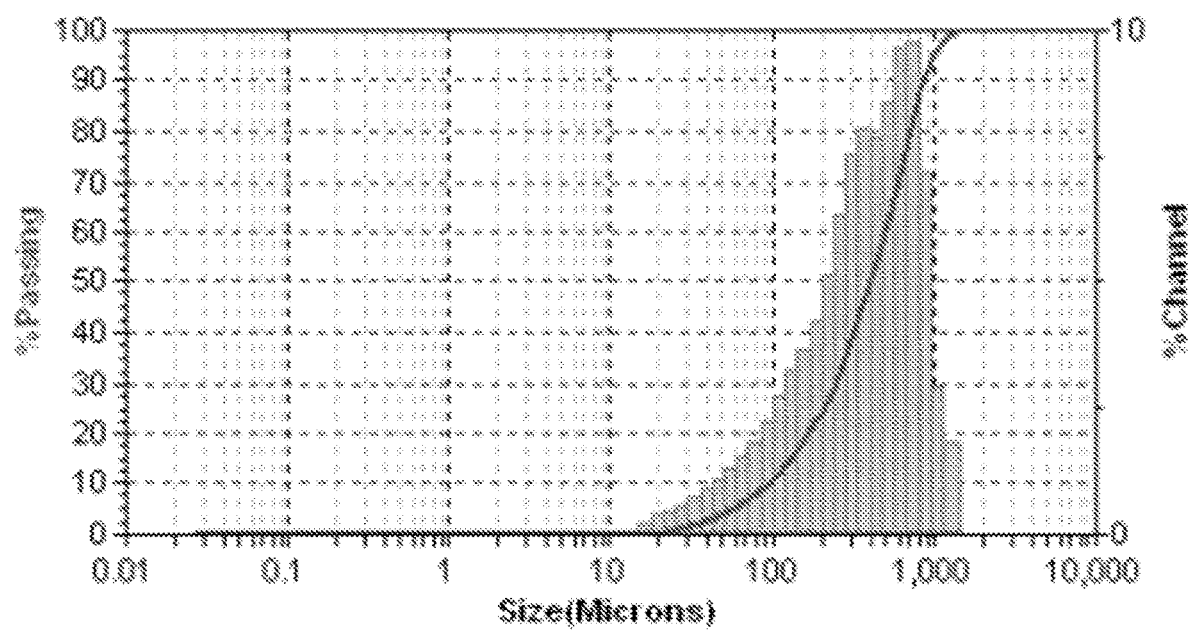
FIG. 1K shows a PSD diagram of the prior art.

The particle size distribution diagrams of Form CS3 and the solid disclosed in prior art are shown in FIGS. 1J and 1K. As shown in FIG. 1J, Form CS3 has a narrow, nearly normal and uniform. Whereas, the solid disclosed in prior art has a large particle size and poor uniformity.

Example 2

Preparation of Form CS2 Example 1:

As shown in Table 2A, certain amount of compound (I) was dissolved in corresponding volume of solvent, and then filtered. The glass vial with filtrate was placed into a 20 mL glass vial with 5.0 mL of acetonitrile (ACN). The 20 mL glass vial was sealed and placed until solid crystallized. The obtained solids were labeled as sample 2-a~2-c.

TABLE 2A

| Sample ID | Mass (mg) | Solvent (v/v) | Volume (mL) |
|---|---|---|---|
| 2-a | 32.6 | EtOH/Acetone 1:1 | 1.5 |
| 2-b | 55.9 | EtOH/Acetone 1:1 | 2.0 |
| 2-c | 25.7 | MeOH | 1.4 |

Preparation of Form CS2 Example 2:

Approximately 5.3 mg of compound (I) was weighed into a 3 mL glass vial followed by adding 2.0 mL of ACN to form a suspension. The suspension was stirred at RT for 5 days and centrifuged. The obtained solids were labeled as sample 2-d.

Figure 2A:
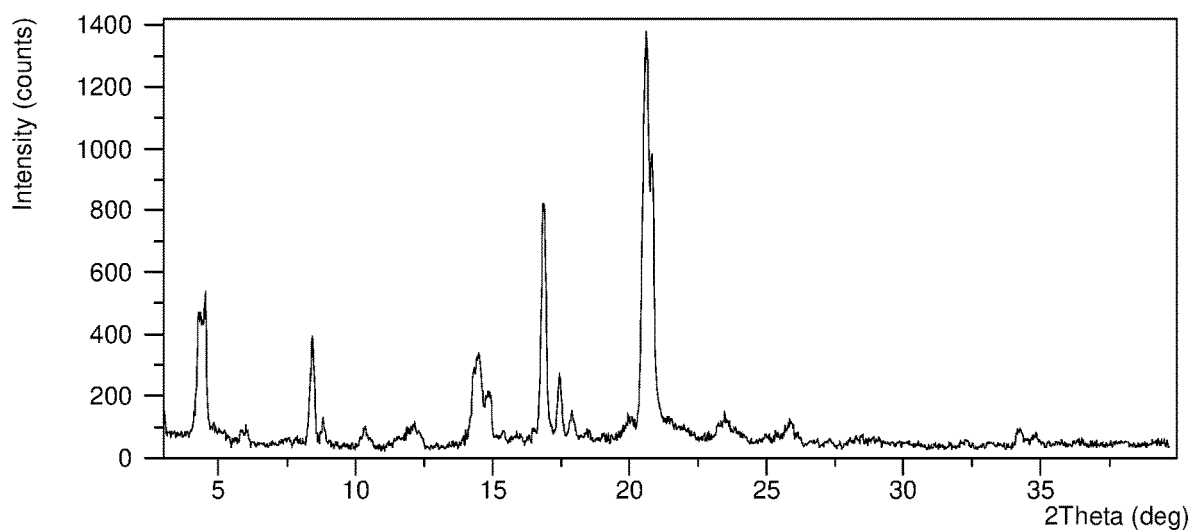
FIG. 2A shows an XRPD pattern of Form CS2 of the present disclosure.

Sample 2-a~2-d were confirmed to be Form CS2 by XRPD. The XRPD pattern of sample 2-a is depicted in FIG. 2A, and the XRPD data are listed in Table 2B. The XRPD patterns of sample 2-b~2-d are the same as or similar to that of sample 2-a.

TABLE 2B

| 2θ | d spacing | Intensity % |
|---|---|---|
| 2.91 | 30.32 | 8.71 |
| 4.27 | 20.70 | 32.29 |
| 4.54 | 19.48 | 37.12 |
| 5.95 | 14.86 | 3.73 |
| 8.45 | 10.47 | 27.43 |
| 8.84 | 10.00 | 5.88 |
| 10.35 | 8.54 | 4.46 |
| 12.25 | 7.22 | 3.82 |
| 14.32 | 6.18 | 19.12 |
| 14.52 | 6.10 | 22.19 |
| 14.94 | 5.93 | 12.78 |
| 16.81 | 5.27 | 56.15 |
| 17.45 | 5.08 | 17.20 |
| 17.90 | 4.96 | 8.29 |
| 20.65 | 4.30 | 100.00 |
| 20.85 | 4.26 | 71.33 |
| 23.50 | 3.79 | 6.83 |
| 25.84 | 3.45 | 5.63 |
| 28.24 | 3.16 | 1.35 |
| 32.26 | 2.78 | 1.11 |
| 34.20 | 2.62 | 3.69 |
| 34.82 | 2.58 | 2.26 |

Figure 2B:
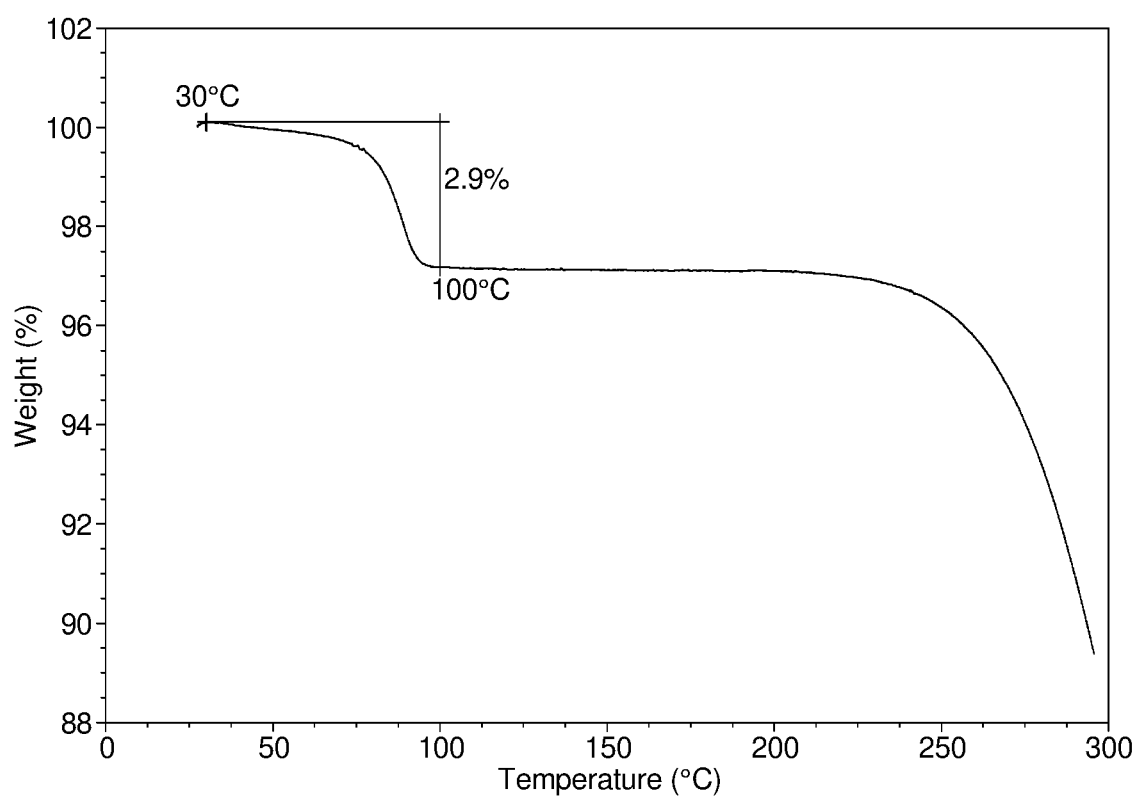
FIG. 2B shows a TGA curve of Form CS2 of the present disclosure.

The TGA curve of Form CS2 shows about 2.9% weight loss when heated to 100° C., which is depicted in FIG. 2B. Form CS2 is a hydrate.

Figure 2C:
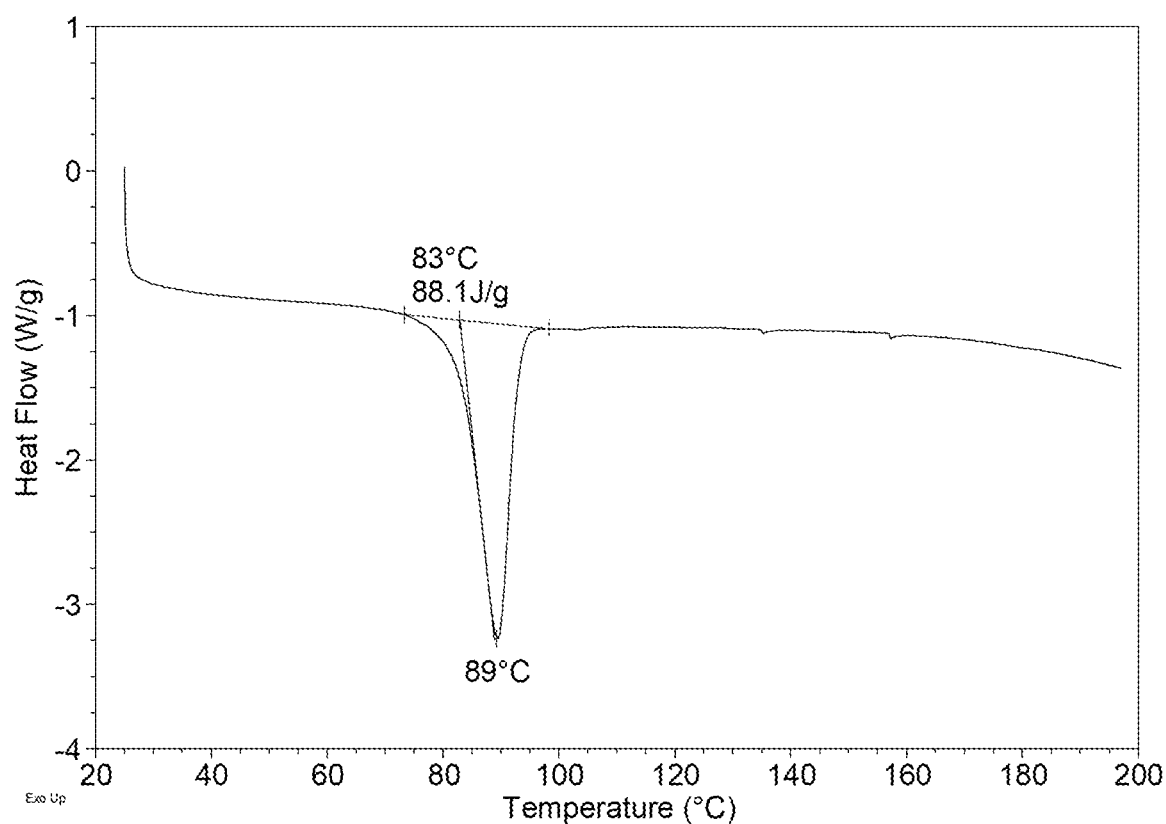
FIG. 2C shows a DSC curve of Form CS2 of the present disclosure.

The DSC curve of Form CS2 is depicted in FIG. 2C, which shows one endothermic peak at around 83° C. (onset temperature).

Hygroscopicity Study of Form CS2

Figure 2D:
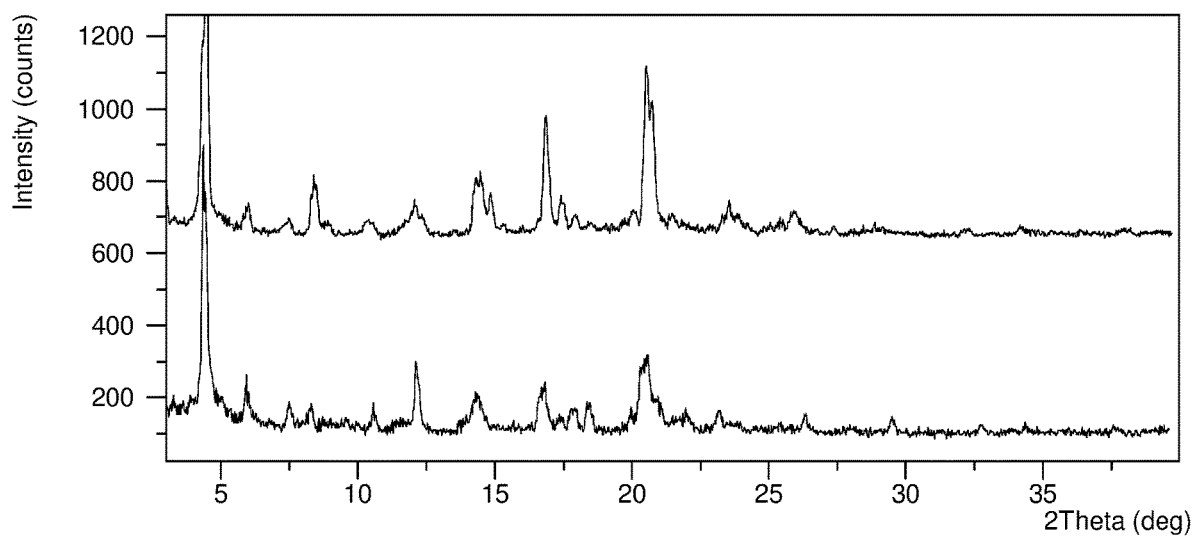
FIG. 2D shows an XRPD pattern overlay of Form CS2 of the present disclosure before and after DVS test, top: XRPD pattern before test, bottom: XRPD pattern after test.

Dynamic vapor sorption (DVS) was applied to test hygroscopicity of Form CS2 with about 10 mg of samples. The results are listed in Table 2C and the XRPD patterns before and after DVS are shown in FIG. 2D. The result shows that weight gain of Form CS2 under 80% RH is 0.46%. Form CS2 is slightly hygroscopic according to the Chinese Pharmacopoeia 2015 edition appendix XIX J Drug hygroscopic test guidelines. As depicted in FIG. 1I, weight gain of the solid disclosed in prior art under 80% RH is 2.44%. The hygroscopicity of Form CS2 is lower than that of prior art. No form change of Form CS2 was observed before and after DVS test.

TABLE 2C

| Sample | Weight gain under 80% Relative Humidity | The definition of hygroscopicity |
| --- | --- | --- |
| Form CS2 | 0.46% | slightly hygroscopic |
| Solid disclosed in CN100386339C | 2.44% | hygroscopic |

Particle Size Study of Form CS2

The particle size distribution of Form CS2 and the solid disclosed in CN100386339C were tested after ultrasonication for 30 seconds. The results are shown in Table 2D. An average particle size of Form CS2 is 41.9 μm, and D90 is 87.5 μm, while the average particle size and D90 of the solid disclosed in prior art are 452.5 μm and 870.3 μm. Compared with prior art, Form CS2 has smaller particle size, which increases the specific surface area of the drug substance, improves the dissolution rate of drug, thereby facilitating drug absorption and further improving the bioavailability of the drug.

TABLE 2D

| Sample | MV (μm) | D10 (μm) | D50 (μm) | D90 (μm) |
| --- | --- | --- | --- | --- |
| Form CS2 | 41.9 | 9.7 | 27.9 | 87.5 |
| Solid disclosed in CN100386339C | 452.5 | 95.0 | 398.8 | 870.3 |

Figure 2E:
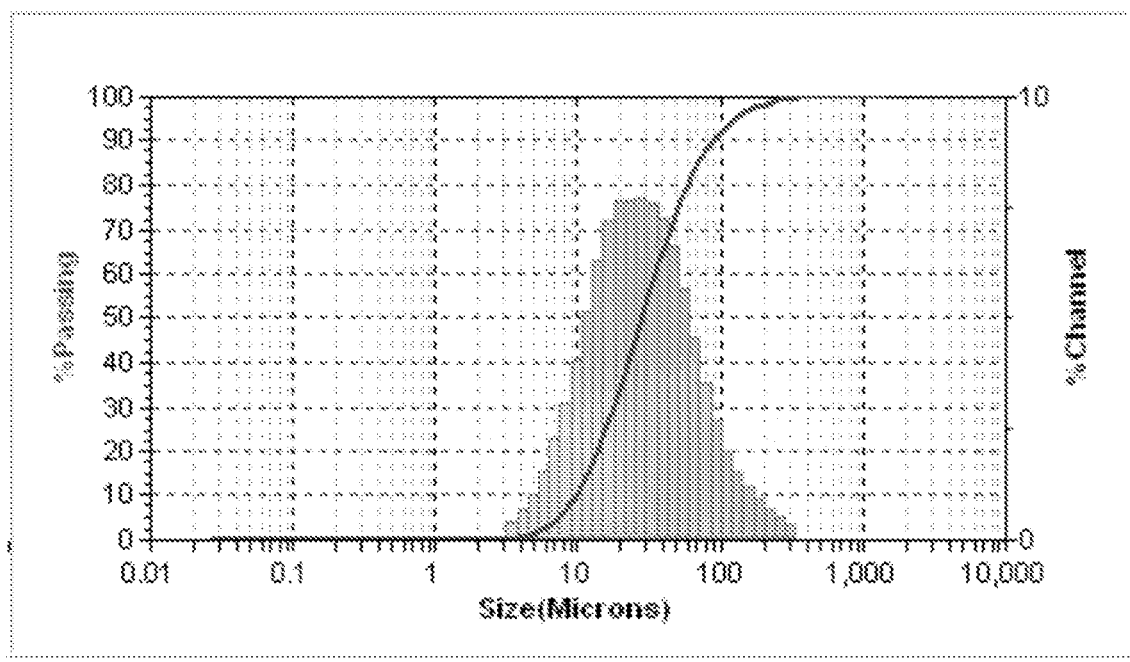
FIG. 2E shows a PSD diagram of Form CS2 of the present disclosure.

The particle size distribution diagrams of Form CS2 and the solid disclosed in prior art are shown in FIGS. 2E and 1K. As shown in FIG. 2E, Form CS2 has a narrow, nearly normal and uniform. Whereas, the solid disclosed in prior art has a large particle size and poor uniformity.

Example 3

Figure 3A:
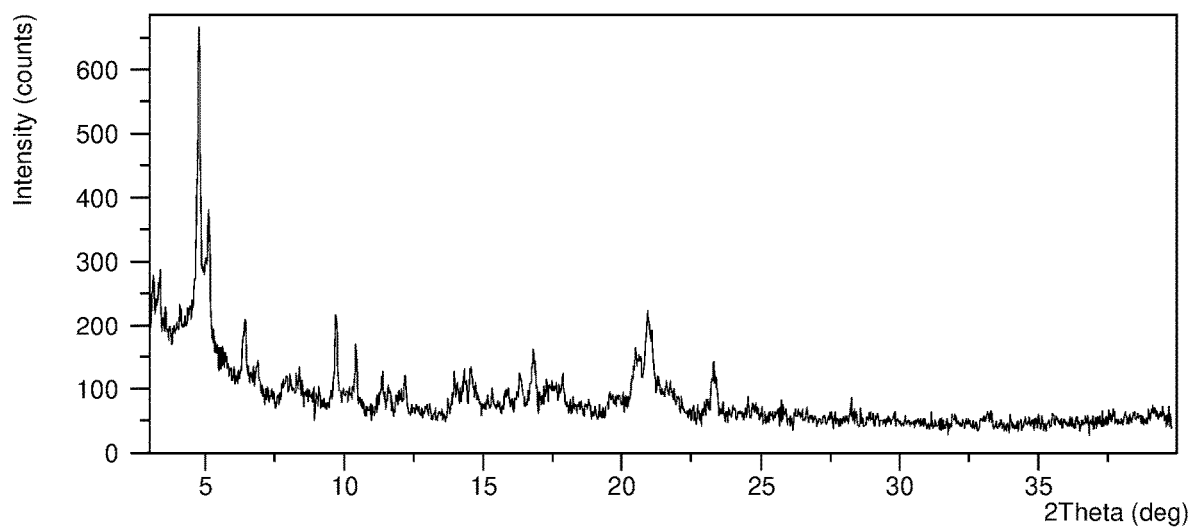
FIG. 3A shows an XRPD pattern of Form CS5 of the present disclosure.

Preparation of Form CS5 Example 1: As shown in Table 3A, certain amount of compound (I) was dissolved in corresponding volume of solvent and then filtered. Then anti-solvent was added into the filtrate drop by drop until a large amount of solid precipitated. The suspension was then centrifuged and solid was obtained. The solid were dried at RT and labeled as sample 3-a~3-c. Sample 3-a~3-c were confirmed to be Form CS5 by XRPD. The XRPD pattern of sample 3-a is depicted in FIG. 3A, and the XRPD data are listed in Table 3B. The XRPD pattern of sample 3-b and 3-c are the same as or similar to that of sample 3-a.

TABLE 3A

| Sample ID | Mass (mg) | Solvent (v/v) | Volume of solvent (mL) | Volume of filtrate (mL) | Anti-solvent | Volume of anti-solvent (mL) |
| --- | --- | --- | --- | --- | --- | --- |
| 3-a | 100.5 | EtOH | 2.0 | 2.0 | ACN | 10.0 |
| 3-b | 92.2 | MeOH | 4.8 | 0.8 | ACN | 3.0 |
| 3-c | 15.8 | IPA | 0.5 | 0.2 | ACN | 2.0 |

TABLE 3B

| 2θ | d spacing | Intensity % |
| --- | --- | --- |
| 3.11 | 28.41 | 35.83 |
| 3.34 | 26.43 | 36.32 |
| 4.76 | 18.57 | 100.00 |
| 5.12 | 17.26 | 56.39 |
| 6.43 | 13.74 | 25.69 |
| 6.88 | 12.85 | 14.22 |
| 7.90 | 11.19 | 9.13 |
| 9.71 | 9.11 | 26.62 |
| 10.43 | 8.48 | 15.50 |
| 11.31 | 7.82 | 6.40 |
| 12.11 | 7.31 | 4.84 |
| 13.96 | 6.34 | 7.31 |
| 14.56 | 6.08 | 11.44 |
| 16.34 | 5.42 | 10.45 |
| 16.82 | 5.27 | 15.50 |
| 17.86 | 4.97 | 10.06 |
| 19.60 | 4.53 | 4.80 |
| 20.51 | 4.33 | 15.06 |
| 20.92 | 4.25 | 25.84 |
| 21.72 | 4.09 | 6.44 |
| 23.30 | 3.82 | 12.46 |
| 28.28 | 3.16 | 2.88 |
| 33.16 | 2.70 | 2.22 |

Figure 3B:
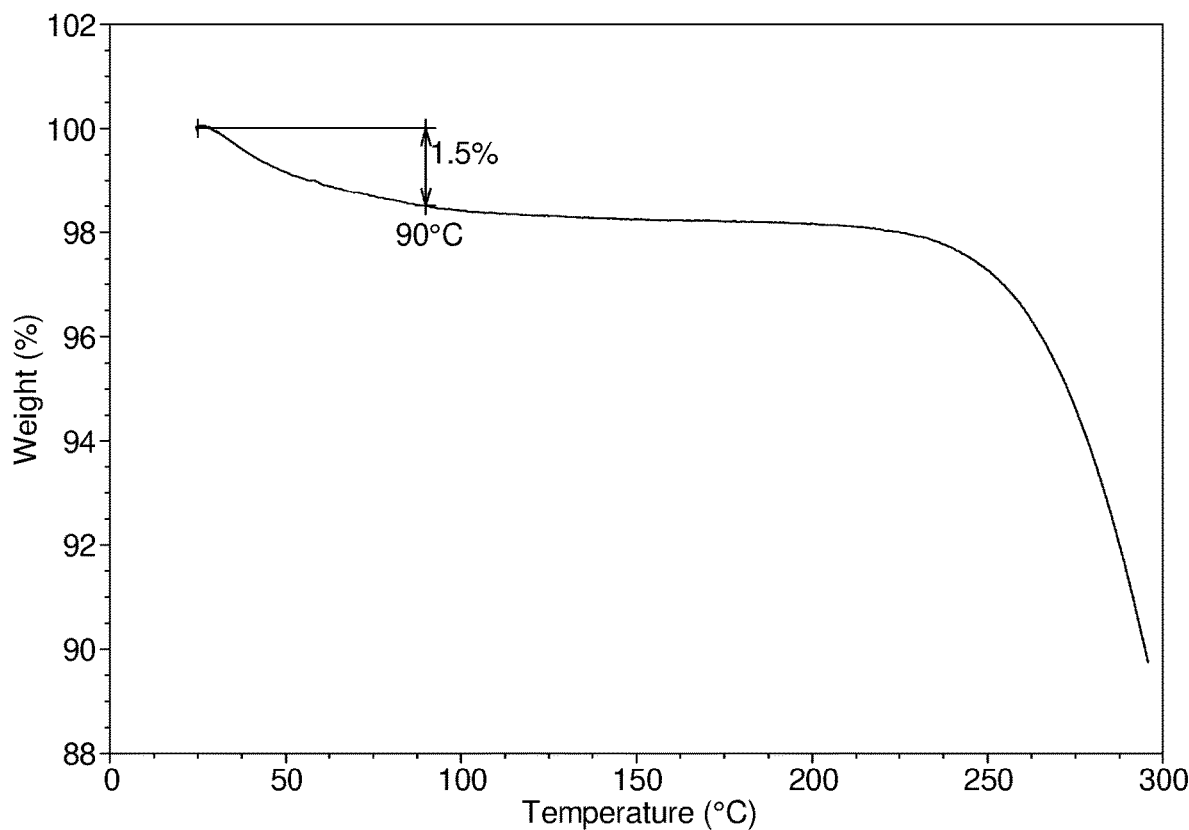
FIG. 3B shows a TGA curve of Form CS5 of the present disclosure.

The TGA curve of Form CS5 shows about 1.5% weight loss when heated to 90° C., which is depicted in FIG. 3B.

Figure 3C:
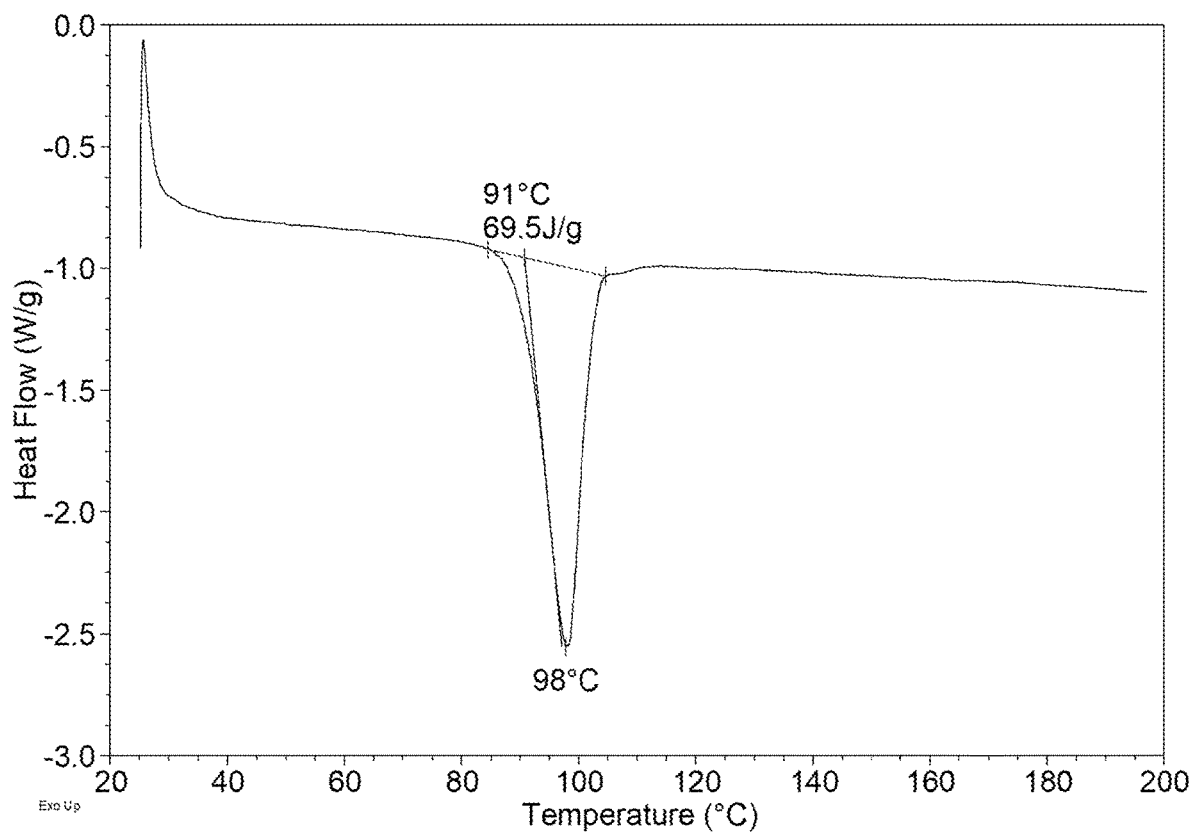
FIG. 3C shows a DSC curve of Form CS5 of the present disclosure.
Figure 3D:
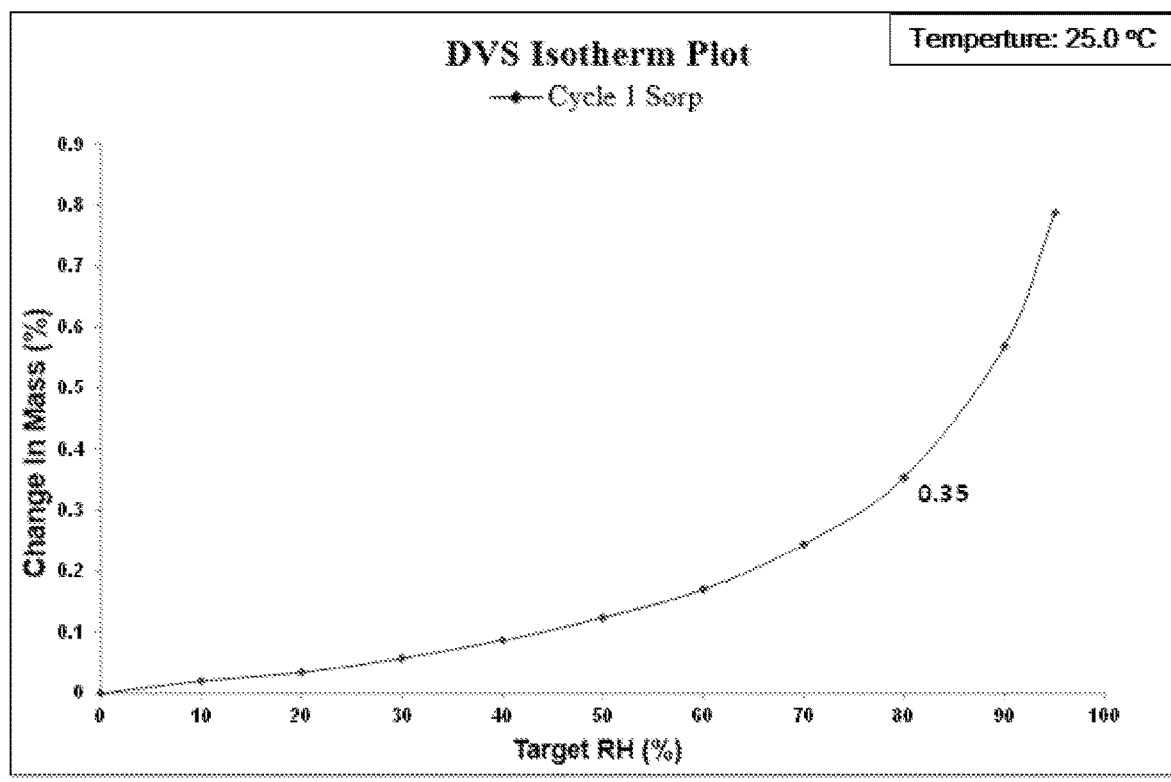
FIG. 3D shows a DVS plot of Form CS5 of the present disclosure.

The DSC curve of Form CS5 is depicted in FIG. 3C, which shows one endothermic peak at around 91° C. (onset temperature).

Hygroscopicity Study of Form CS5

Dynamic vapor sorption (DVS) was applied to test hygroscopicity of Form CS5 with about 8 mg of samples. The results are listed in Table 3C. The result shows that weight gain of Form CS5 under 80% RH is 0.35%. Form CS5 is slightly hygroscopic according to the Chinese Pharmacopoeia 2015 edition appendix XIX J Drug hygroscopic test guidelines. As depicted in FIG. 1I, weight gain of the solid disclosed in prior art under 80% RH is 2.44%. The hygroscopicity of Form CS5 is lower than that of prior art. No form change of Form CS5 was observed before and after DVS test.

TABLE 3C

| Sample | Weight gain under 80% Relative Humidity | The definition of hygroscopicity |
| --- | --- | --- |
| Form CS5 | 0.35% | slightly hygroscopic |
| Solid disclosed in CN100386339C | 2.44% | hygroscopic |

Example 4

Figure 4A:
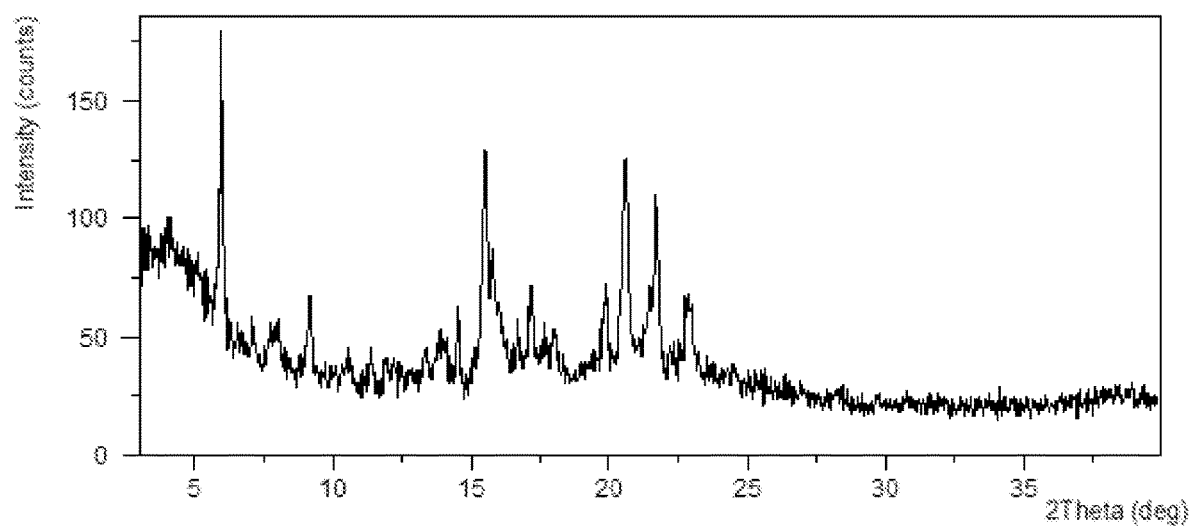
FIG. 4A shows an XRPD pattern of Form CS8 of the present disclosure.
Figure 4B:
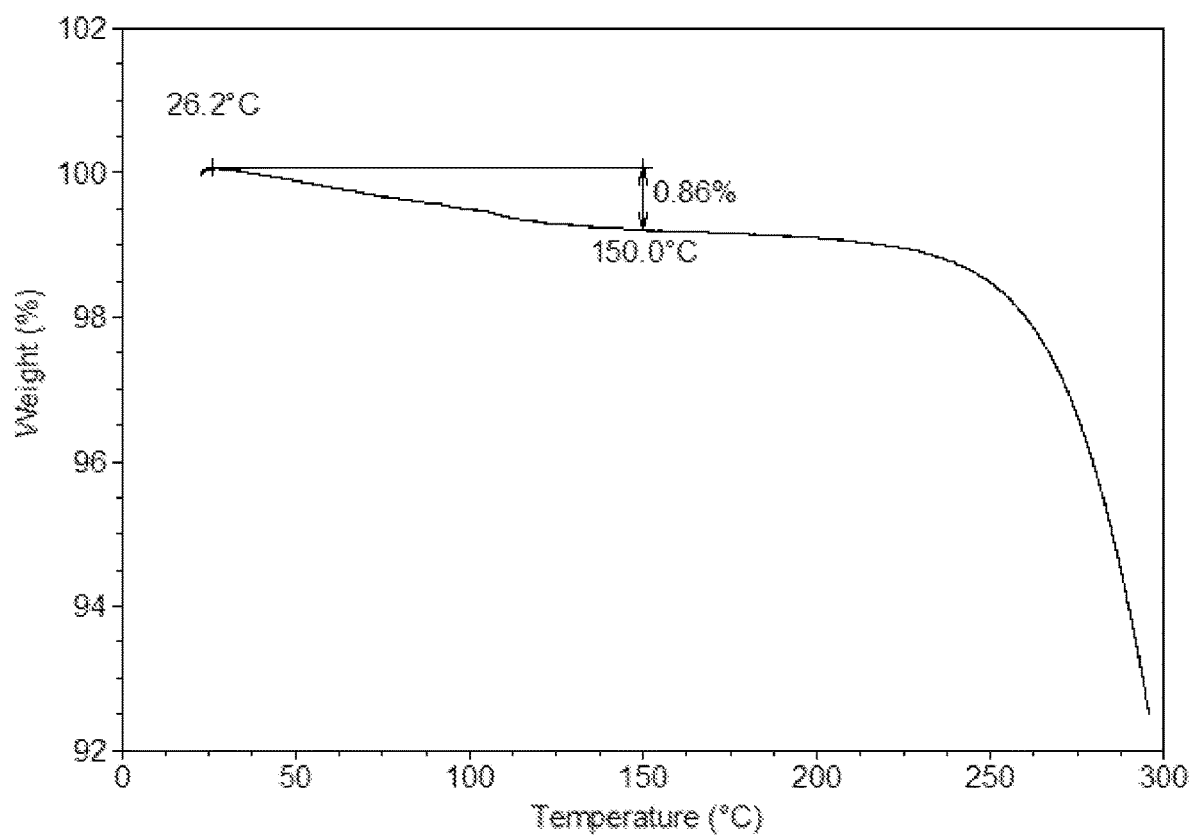
FIG. 4B shows a TGA curve of Form CS8 of the present disclosure.
Figure 4C:
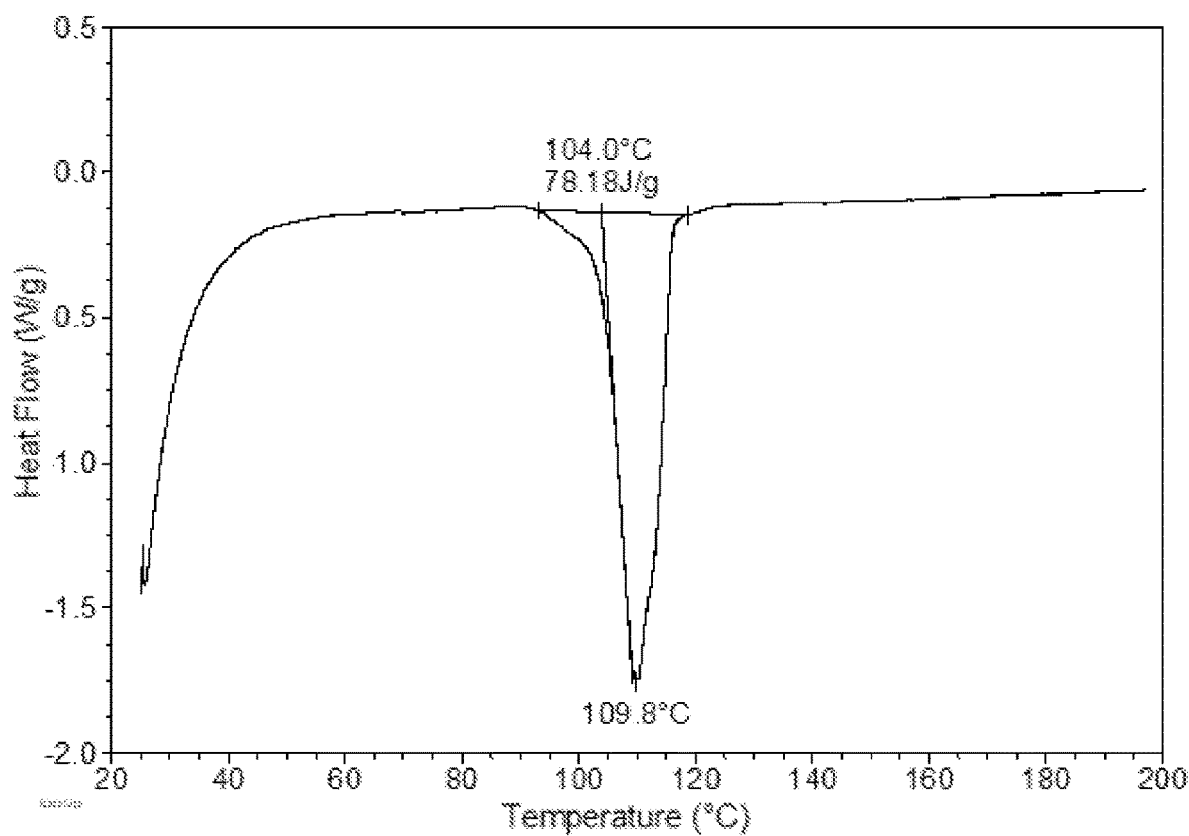
FIG. 4C shows a DSC curve of Form CS8 of the present disclosure.

Preparation of Form CS8 Example 1:

Form CS2 was stored at RT for one month. Then the sample was heated to 95° C. at a rate of 10° C./min with nitrogen purging, held at 95° C. for 2 min, and then cooled to RT at a rate of 5° C./min. The heating and cooling processes were conducted in a TGA equipment. The obtained sample was stored at 60° C./75% RH for one month to get Form CS8. The XRPD pattern of Form CS8 is depicted in FIG. 4A, and the XRPD data are listed in Table 4A. The TGA curve of Form CS8 shows about 0.9% weight loss when heated to 150° C., which is depicted in FIG. 4B. The DSC curve of Form CS8 is depicted in FIG. 4C, which shows one endothermic peak at around 104° C.

TABLE 4A

| 2θ | d spacing | Intensity % |
|---|---|---|
| 5.96 | 14.83 | 100.00 |
| 7.97 | 11.10 | 8.80 |
| 9.19 | 9.62 | 24.41 |
| 10.52 | 8.41 | 6.32 |
| 13.33 | 6.64 | 8.28 |
| 13.92 | 6.36 | 13.11 |
| 14.52 | 6.10 | 20.11 |
| 15.50 | 5.72 | 82.15 |
| 15.76 | 5.62 | 46.17 |
| 16.67 | 5.32 | 21.95 |
| 17.18 | 5.16 | 32.62 |
| 18.00 | 4.93 | 17.41 |
| 18.32 | 4.84 | 10.15 |
| 19.90 | 4.46 | 29.70 |
| 20.60 | 4.31 | 78.93 |
| 21.71 | 4.09 | 66.13 |
| 22.80 | 3.90 | 28.42 |
| 22.96 | 3.87 | 27.23 |

Preparation of Form CS8 Example 2:

Form CS2 was stored at 25° C./60% RH for one week. The obtained sample was heated to 95° C. at a rate of 10° C./min with nitrogen purging, held at 95° C. for 2 min, and then cooled to RT at a rate of 10° C./min. The heating and cooling processes were conducted in a TGA equipment. Form CS8 was obtained and the XRPD data are listed in Table 4B.

TABLE 4B

| 2θ | d spacing | Intensity % |
|---|---|---|
| 4.09 | 21.62 | 7.54 |
| 5.99 | 14.75 | 100.00 |
| 8.05 | 10.99 | 4.17 |
| 9.08 | 9.74 | 9.59 |
| 10.63 | 8.32 | 3.40 |
| 14.07 | 6.29 | 9.73 |
| 14.68 | 6.03 | 7.68 |
| 15.56 | 5.69 | 30.89 |
| 15.84 | 5.60 | 34.75 |
| 16.33 | 5.43 | 16.70 |
| 16.72 | 5.30 | 11.72 |
| 17.20 | 5.16 | 15.53 |
| 17.73 | 5.00 | 17.76 |
| 19.95 | 4.45 | 15.46 |
| 20.67 | 4.30 | 22.07 |
| 21.45 | 4.14 | 17.26 |
| 21.79 | 4.08 | 15.35 |
| 22.87 | 3.89 | 11.37 |

Stability Study of Form CS8

As active pharmaceutical ingredient plays an important part in drug products, it is vital that the crystalline active pharmaceutical ingredient has good physical and chemical stability. Good physical stability avoids crystal transformation during the storage and formulation processes, thereby ensuring consistent and controllable quality of the drug substance and drug product.

Figure 4D:
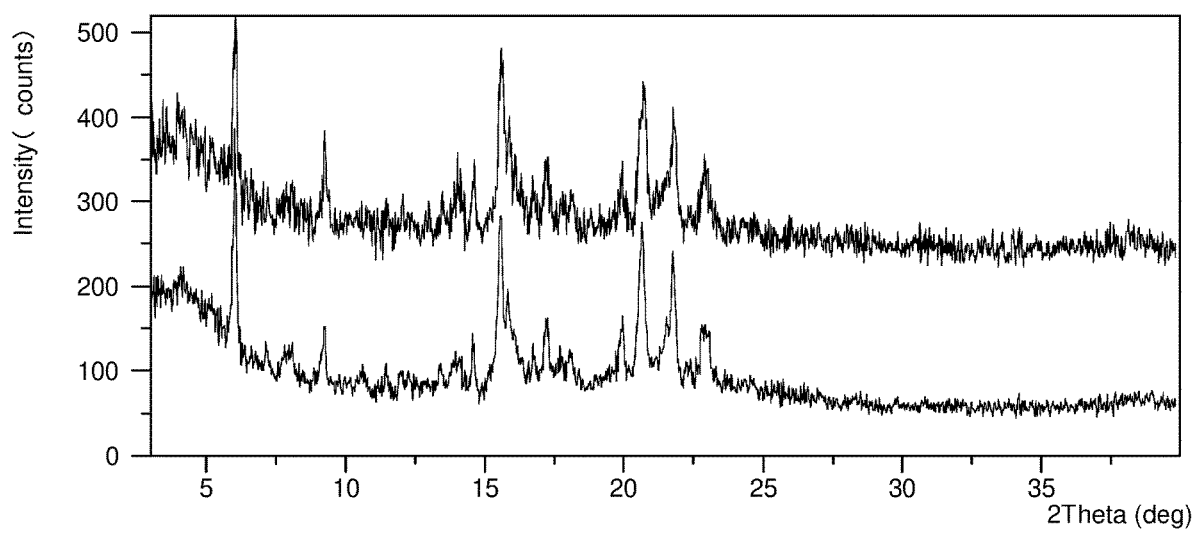
FIG. 4D shows an XRPD pattern overlay of Form CS8 of the present disclosure before and after being stored under 60° C./75% RH for 3 weeks, top: XRPD pattern before storage, bottom: XRPD pattern after storage.

Form CS8 were stored in open dishes under 25° C./60% RH, 40° C./75% RH and 60° C./75% RH conditions for three weeks, and sampled for XRPD test. The results showed that no form change was observed, and the XRPD data of the sample before and after stored 60° C./75% RH for three weeks are shown in FIG. 4D as a representative.

Form CS8 is stable for at least three weeks under 25° C./60% RH, 40° C./75% RH and 60° C./75% RH. Further, Form CS8 is stable for at least three months. Further, Form CS8 is stable for at least six months. Further, Form CS8 is stable for at least one year. The results show that Form CS8 has good stability and is suitable for drug development.

Hygroscopicity Study of Form CS8

Figure 4E:
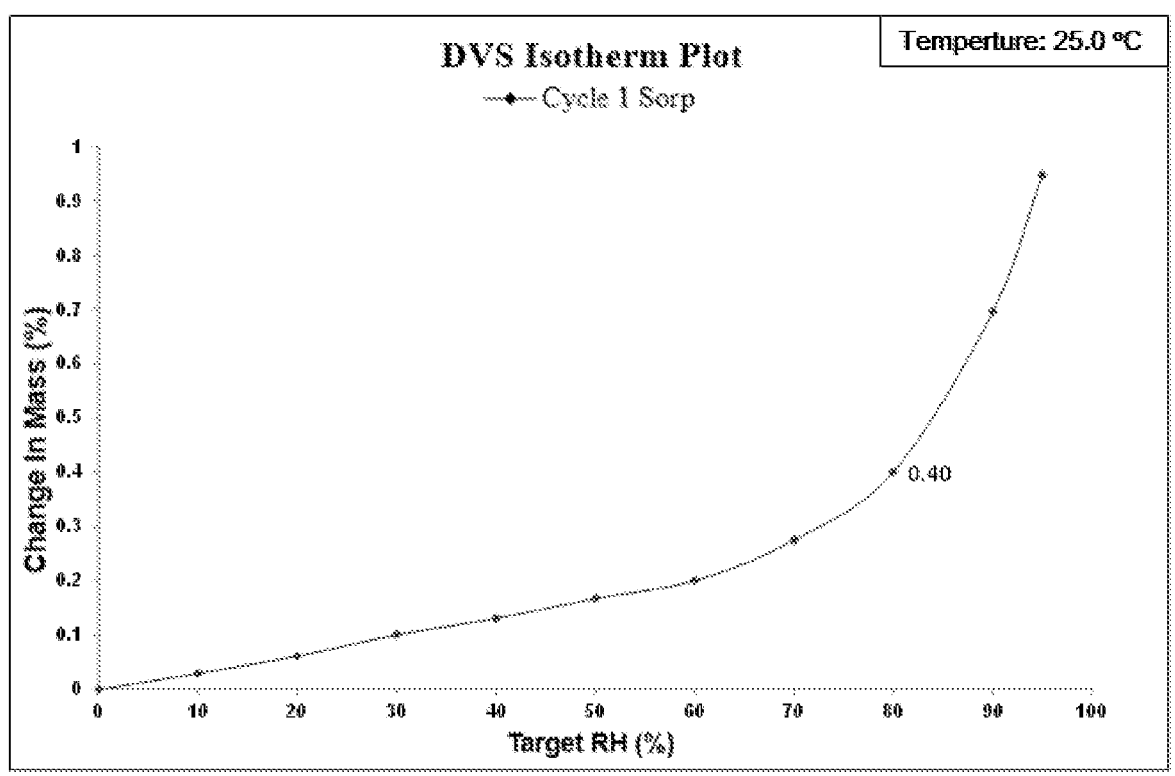
FIG. 4E shows a DVS plot of Form CS8 of the present disclosure.
Figure 4F:
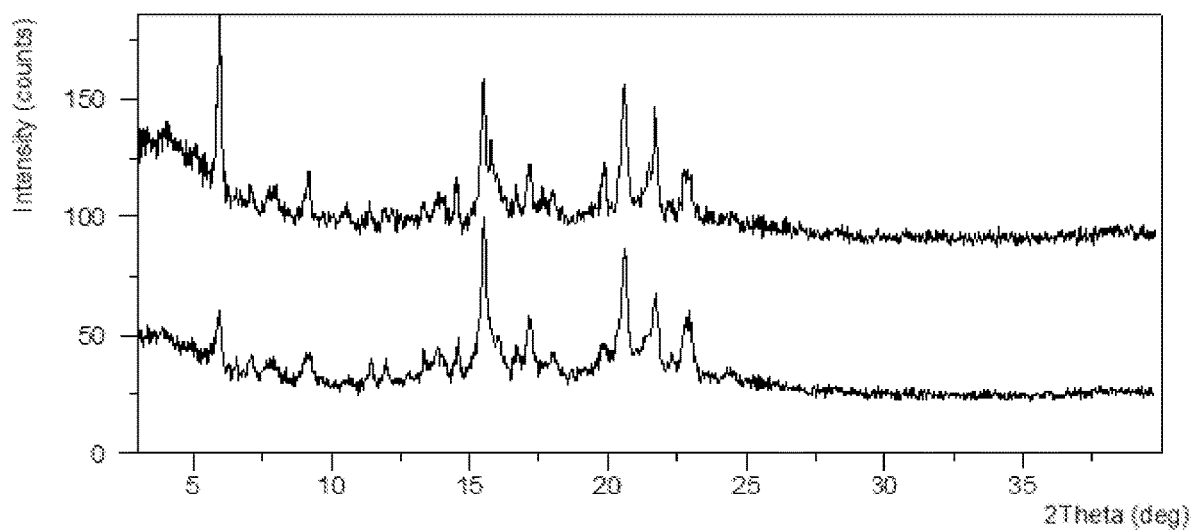
FIG. 4F shows an XRPD pattern overlay of Form CS8 of the present disclosure before and after DVS test, top: XRPD pattern before test, bottom: XRPD pattern after test.

Dynamic vapor sorption (DVS) was applied to test hygroscopicity of Form CS8 with about 7 mg of sample. The results were listed in Table 4C and DVS curve is shown in FIG. 4E. The result showed that the weight gain of Form CS8 under 80% RH is 0.40%. Form CS8 is slightly hygroscopic according to the Chinese Pharmacopoeia 2015 edition appendix XIX J Drug hygroscopic test guidelines. As depicted in FIG. 1I, weight gain of the solid disclosed in prior art under 80% RH is 2.44%. The hygroscopicity of Form CS8 is lower than that of prior art. No form change of Form CS8 was observed before and after DVS test. The XRPD patterns before and after DVS were shown in FIG. 4F, top: the XRPD pattern before DVS; bottom: XRPD pattern after DVS.

TABLE 4C

| Sample | Weight gain under 80% Relative Humidity | The definition of hygroscopicity |
|---|---|---|
| Form CS8 | 0.40% | Slightly hygroscopic |
| Solid disclosed in CN100386339C | 2.44% | Hygroscopic |

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

The invention claimed is:

1. A crystalline form CS3 of compound (I), wherein the X-ray powder diffraction pattern shows characteristic peaks at 2theta values of 20.5°±0.2°, 15.4°±0.2°, 22.3°±0.2°, 7.8°±0.2°, 17.0°±0.2°, and 17.9°±0.2° using CuKα radiation

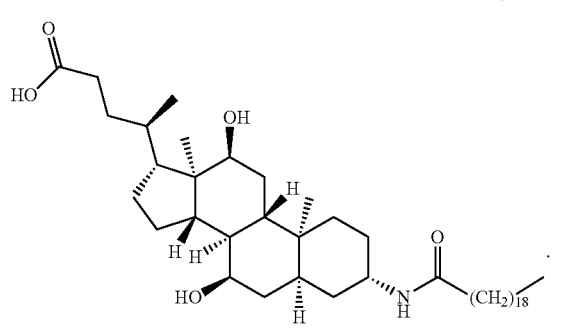

Compound (I)

2. The crystalline form CS3 according to claim 1, wherein the X-ray powder diffraction pattern shows one or two or three characteristic peaks at 2theta values of 8.4°±0.2°, 5.1°±0.2° and 19.1°±0.2° using CuKα radiation.

3. A process for preparing crystalline form CS3 according to claim 1, wherein the process comprises:

1) Suspending a solid of compound (I) into a solvent mixture comprising an alcohol and water or an alcohol and an ester, then, stirring the solution at 0-80° C. to obtain crystalline form CS3; or 2) Adding a solid of compound (I) into a solvent to obtain a solution of compound (I), and adding an anti-solvent slowly into the solution of compound (I), wherein the solvent is a halogenated hydrocarbon, and the anti-solvent is an aromatic hydrocarbon; or adding the solution of compound (I) into an anti-solvent, wherein the solvent is an ether, and the anti-solvent is an alkane, and stirring at room temperature to obtain a crystalline form CS3.

4. The process for preparing crystalline form CS3 according to claim 3, wherein in method 1) said mixture of the alcohol and water is a mixture of isopropanol and water, said mixture of the alcohol and the ester is a mixture of isopropanol and isopropyl acetate, and in method 2) said halogenated hydrocarbon is chloroform, said aromatic hydrocarbon is toluene, said ether is tetrahydrofuran or 2-methyltetrahydrofuran, and said alkane is n-heptane.

5. A crystalline form CS2 of compound (I), wherein the X-ray powder diffraction pattern shows characteristic peaks at 2theta values of 20.5°±0.2°, 16.8°±0.2°, 4.3°±0.2°, 8.4°±0.2°, 17.6°±0.2°, and 14.9°±0.2° using CuKα radiation

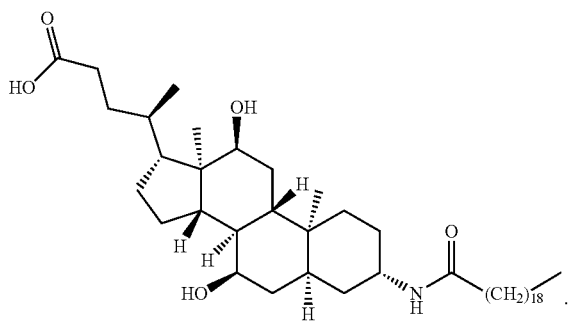

Compound (I)

6. A process for preparing crystalline form CS2 according to claim 5, wherein the process comprises:

1) Mixing a solid of compound (I) with methanol or a solvent mixture of ethanol and acetone, filtering after dissolved, and storing the filtrate in a larger sealed device containing acetonitrile at 0-30° C. to obtain crystalline form CS2; or 2) Suspending a solid of compound (I) into acetonitrile, then stirring the solution at 0-30° C. to obtain crystalline form CS2.

7. A crystalline form CS5 of compound (I), wherein the X-ray powder diffraction pattern shows characteristic peaks at 2theta values of 4.8°±0.2°, 9.7°±0.2°, 6.4°±0.2°, 20.9°±0.2°, 16.8°±0.2°, 23.3°±0.2°, and 14.6°±0.2° using CuKα radiation

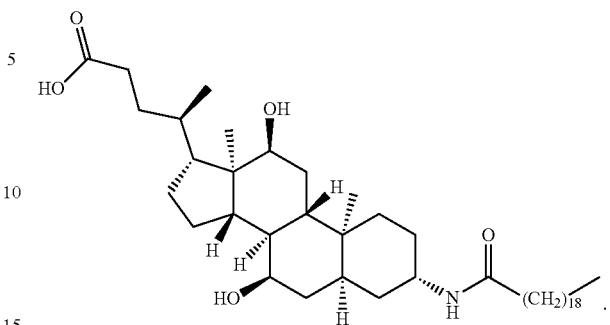

Compound (I)

8. A process for preparing crystalline form CS5 according to claim 7, wherein the process comprises:

Adding a solid of compound (I) into a solvent selected from an alcohol to obtain a solution of compound (I), and adding acetonitrile slowly into the solution of compound (I), stirring at room temperature until solid precipitates, then, separating and drying to obtain crystalline form CS5.

9. The process for preparing crystalline form CS5 according to claim 8, wherein said alcohol is methanol, ethanol or isopropanol.

10. A crystalline form CS8 of compound (I), wherein the X-ray powder diffraction pattern shows characteristic peaks at 2theta values of 6.0°±0.2°, 15.5°±0.2°, 20.7°±0.2°, 21.8°±0.2°, 9.1°±0.2°, 19.9°±0.2°, and 22.9°±0.2° using CuKα radiation

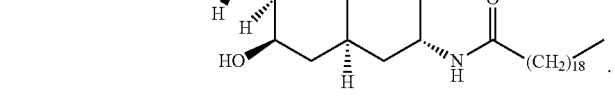

Compound (I)

11. A process for preparing crystalline form CS8 according to claim 10, wherein the process comprises:

Storing crystalline form CS2 at room temperature for 7-30 days, heating the obtained sample to 95° C. ±2° C. at a rate of 5-20° C./min with nitrogen purging, holding at 95° C. ±2° C. for 1-10 min, and then cooling to room temperature at a rate of 5-20° C./min to obtain crystalline form CS8.

12. A pharmaceutical composition, wherein said pharmaceutical composition comprises a crystalline form CS3 according to claim 1, and a pharmaceutically acceptable carrier, a diluent or an excipient.

13. A method for treating non-alcoholic steatohepatitis, gallstones, cholesterol gallstone, or atherosclerosis, comprising administering to a patient in need thereof a therapeutically effective amount of crystalline form CS3 according to claim 1.

14. A method for treating non-alcoholic steatohepatitis, gallstones, cholesterol gallstone, or atherosclerosis, comprising administering to a patient in need thereof a therapeutically effective amount of crystalline form CS2 according to claim 5.

15. A method for treating non-alcoholic steatohepatitis, gallstones, cholesterol gallstone, or atherosclerosis, comprising administering to a patient in need thereof a therapeutically effective amount of crystalline form CS5 according to claim 7.

16. A method for treating non-alcoholic steatohepatitis, gallstones, cholesterol gallstone, or atherosclerosis, comprising administering to a patient in need thereof a therapeutically effective amount of crystalline form CS8 according to claim 10.

17. A pharmaceutical composition, wherein said pharmaceutical composition comprises a crystalline form CS2 according to claim 5, and a pharmaceutically acceptable carrier, a diluent or an excipient.

18. A pharmaceutical composition, wherein said pharmaceutical composition comprises a crystalline form CS5 according to claim 7, and a pharmaceutically acceptable carrier, a diluent or an excipient.

19. A pharmaceutical composition, wherein said pharmaceutical composition comprises a crystalline form CS8 according to claim 10, and a pharmaceutically acceptable carrier, a diluent or an excipient.

\* \* \* \* \*